United States Patent
Mohr et al.

(10) Patent No.: US 9,796,642 B2
(45) Date of Patent: Oct. 24, 2017

(54) PNEUMATICALLY AGITATED IONIC LIQUID ALKYLATION USING VAPORIZATION TO REMOVE REACTION HEAT

(71) Applicant: Chevron U.S.A. Inc., San Ramon, CA (US)

(72) Inventors: Donald Henry Mohr, Orinda, CA (US); Huping Luo, Richmond, CA (US); Clifford Michael Lowe, Moraga, CA (US); Hye Kyung Cho Timken, Albany, CA (US); Krishniah Parimi, Alamo, CA (US); Michael John Girgis, Richmond, CA (US); Bong-Kyu Chang, Novato, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 261 days.

(21) Appl. No.: 14/656,967

(22) Filed: Mar. 13, 2015

(65) Prior Publication Data

US 2016/0264494 A1 Sep. 15, 2016

(51) Int. Cl.
*C07C 2/58* (2006.01)
*C10G 29/20* (2006.01)
*C07C 9/00* (2006.01)

(52) U.S. Cl.
CPC ............. *C07C 2/58* (2013.01); *C10G 29/205* (2013.01); *C10G 2300/1088* (2013.01)

(58) Field of Classification Search
CPC .. C07C 2/58; C10G 29/205; C10G 2300/1088
See application file for complete search history.

(56) References Cited

U.S. PATENT DOCUMENTS

| 4,218,575 | A | 8/1980 | Webb |
| 4,225,742 | A * | 9/1980 | Hutson, Jr. ............... C07C 2/62 585/723 |
| 5,292,981 | A * | 3/1994 | Huang ...................... B01J 8/20 502/34 |
| 5,856,606 | A | 1/1999 | Oroskar |
| 8,222,471 | B2 | 7/2012 | Elomari et al. |
| 2009/0171133 | A1 | 7/2009 | Luo et al. |

(Continued)

FOREIGN PATENT DOCUMENTS

EP 0 057 659 A2 8/1982

OTHER PUBLICATIONS

Xing, X. et al., Isobutane alkylation using acidic ionic liquid catalysts., Catalyst Communications. 2012. vol. 26, pp. 68-71.

(Continued)

*Primary Examiner* — Brian McCaig
*Assistant Examiner* — Jason Chong
(74) *Attorney, Agent, or Firm* — Susan M. Abernathy

(57) ABSTRACT

Systems and apparatus for ionic liquid catalyzed hydrocarbon conversion, such as alkylation, using vaporization to remove reaction heat from an ionic liquid reactor and to provide mixing therein, wherein hydrocarbon vapors are withdrawn from the ionic liquid reactor and the withdrawn hydrocarbon vapor is recovered by a hydrocarbon vapor recovery unit in fluid communication with the ionic liquid reactor for recycling condensed hydrocarbons to the ionic liquid reactor. Processes for ionic liquid catalyzed alkylation are also disclosed.

27 Claims, 17 Drawing Sheets

(56) References Cited

U.S. PATENT DOCUMENTS

2011/0319695 A1 12/2011 Hommeltoft et al.
2013/0066130 A1 3/2013 Luo et al.

OTHER PUBLICATIONS

Al-Azzi, et al., Influence of Draft Tube Diameter on Operation Behavior of Air Loop Reactors, Al-Khwarizmi Engineering Journal, vol. 6, No. 2, pp. 21-32 (2010).

* cited by examiner

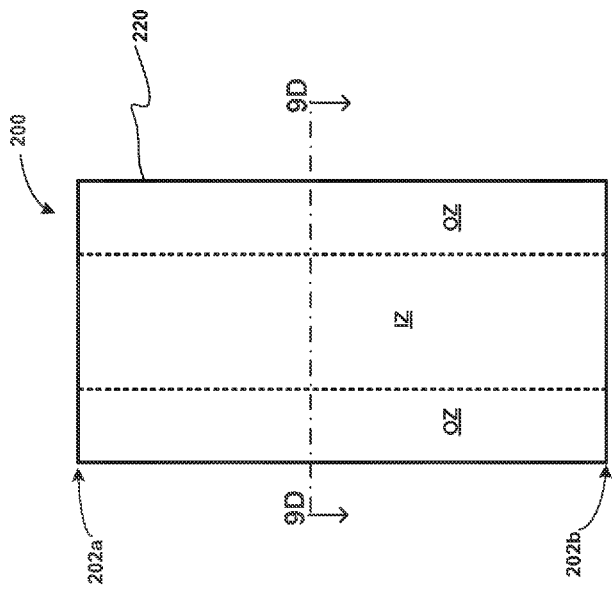
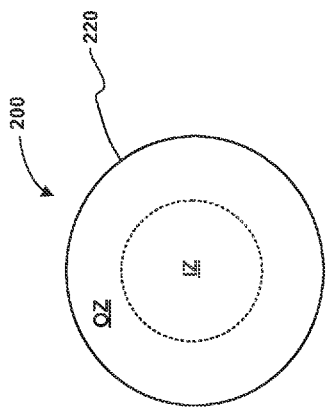
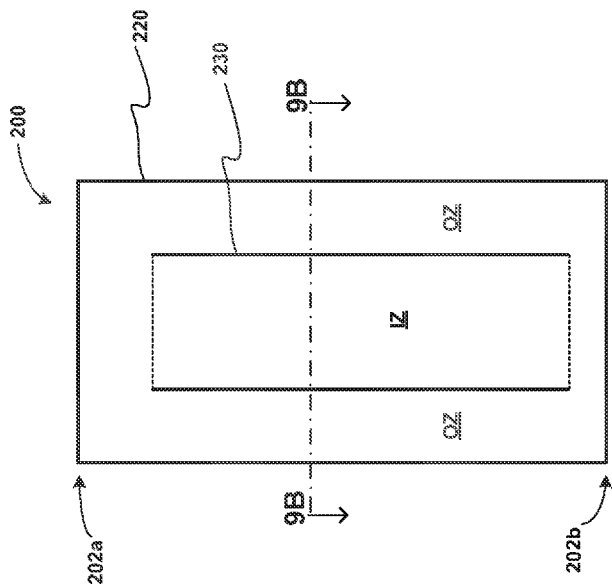
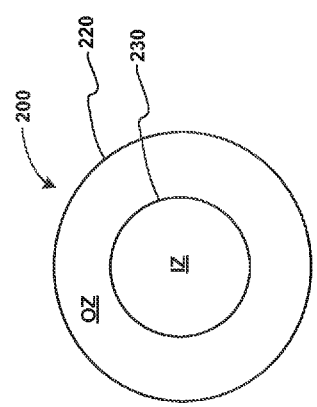

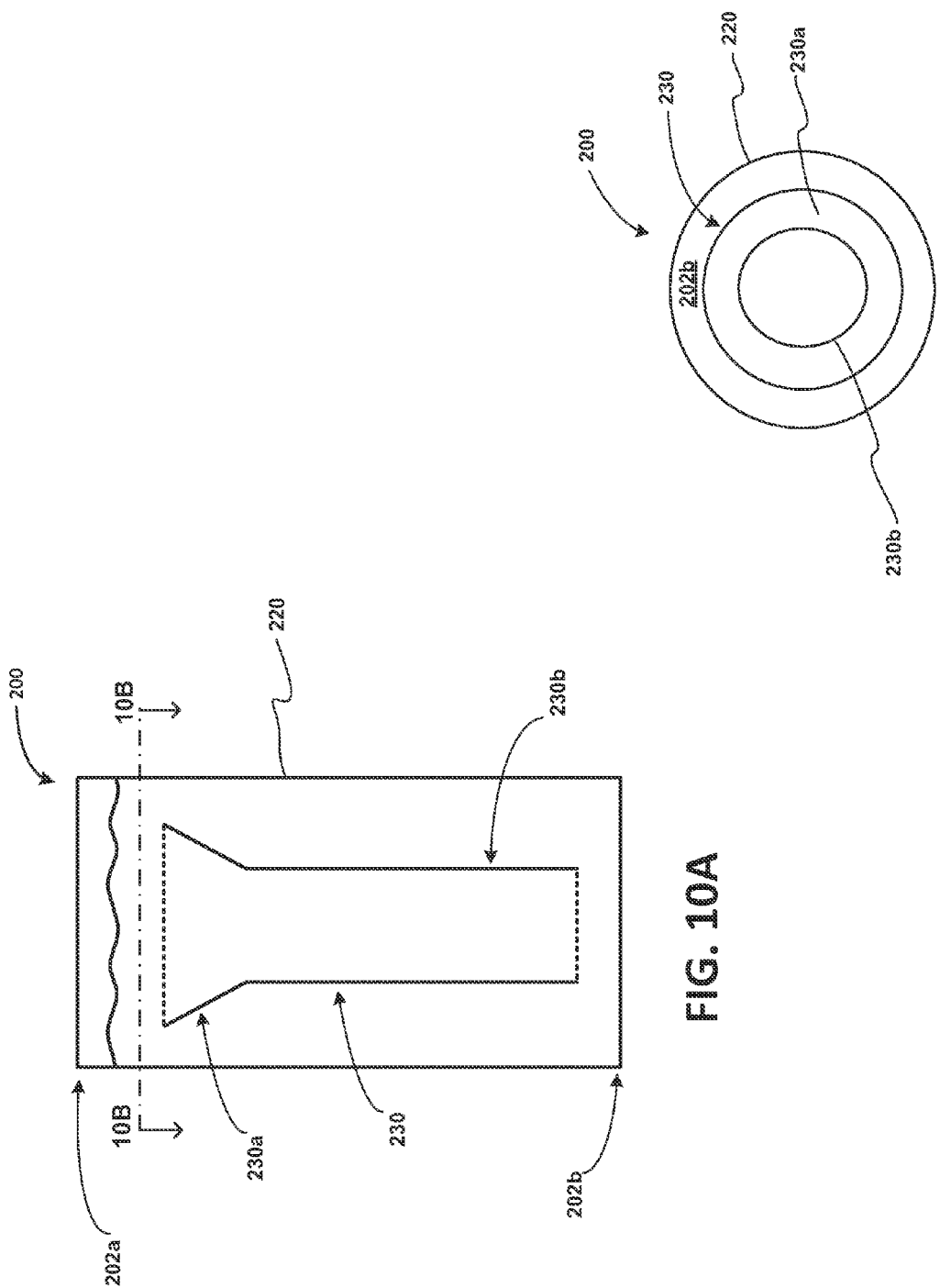

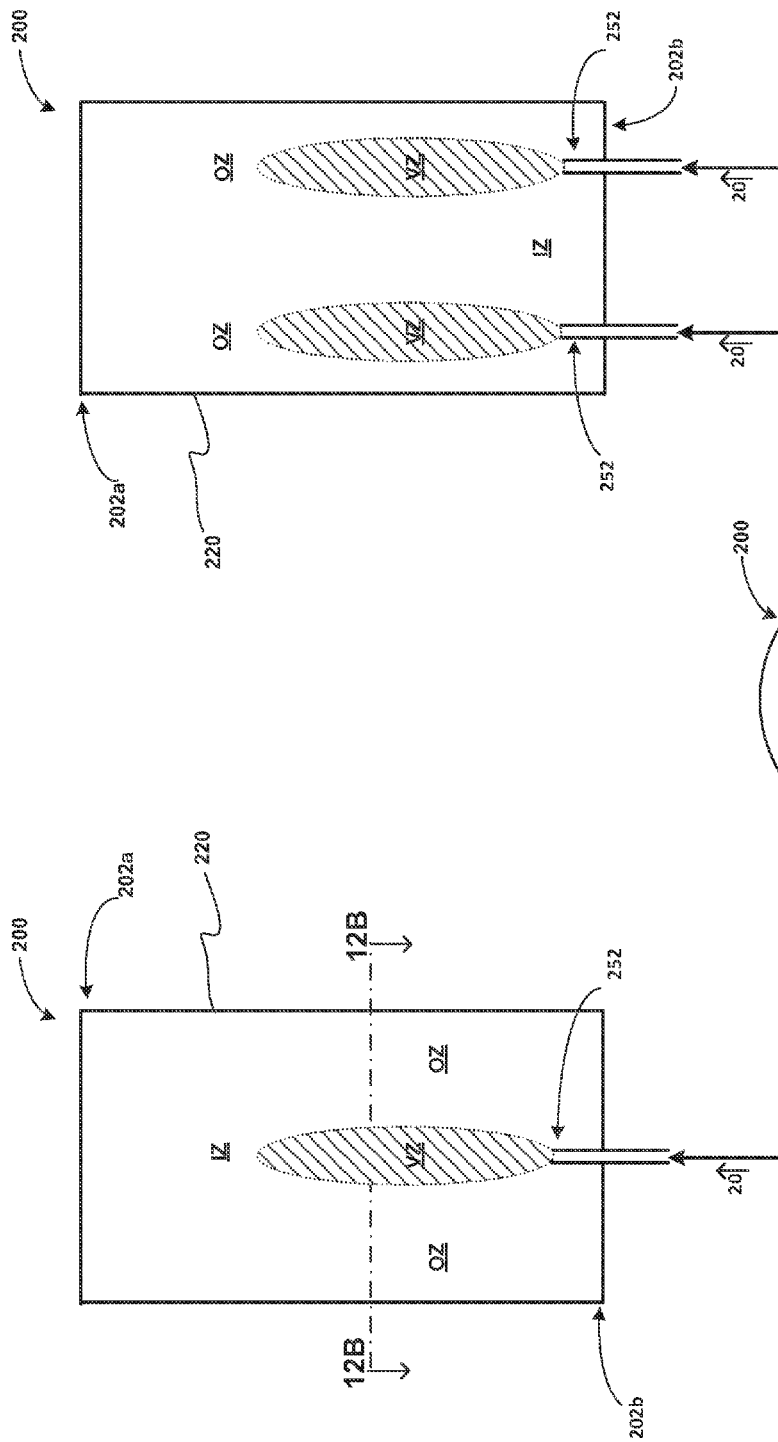

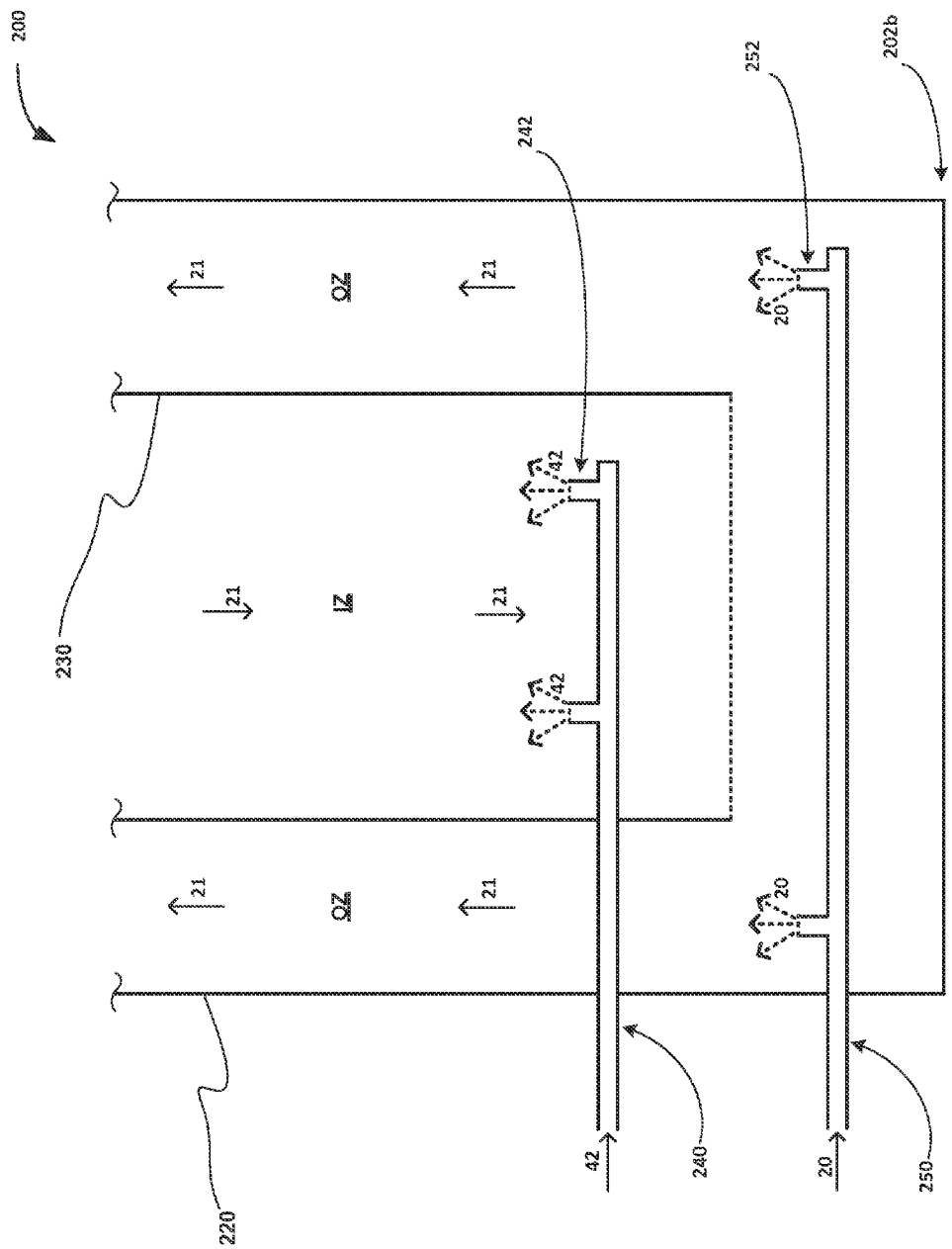

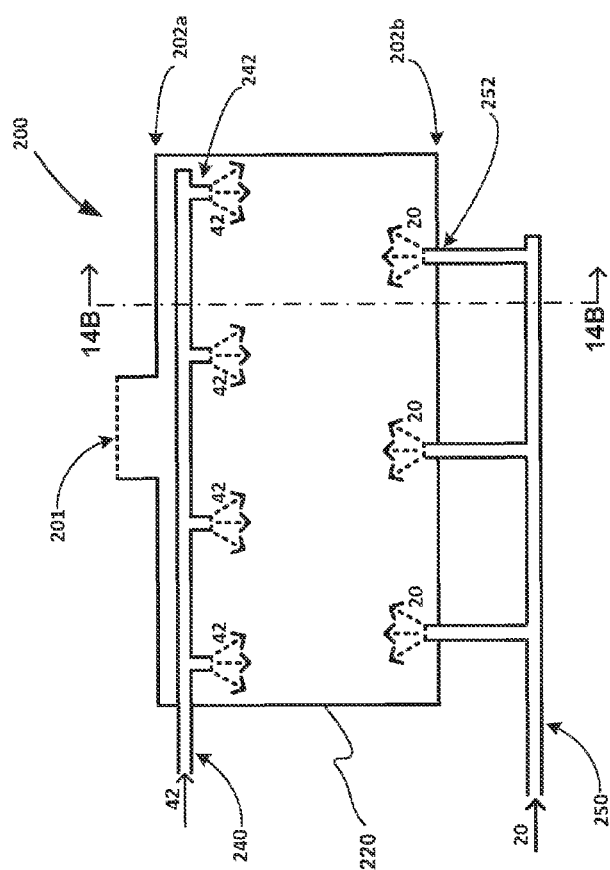
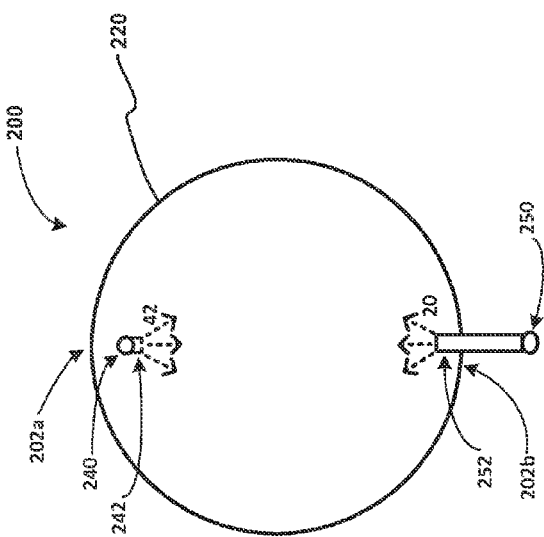
FIG. 14A
FIG. 14B

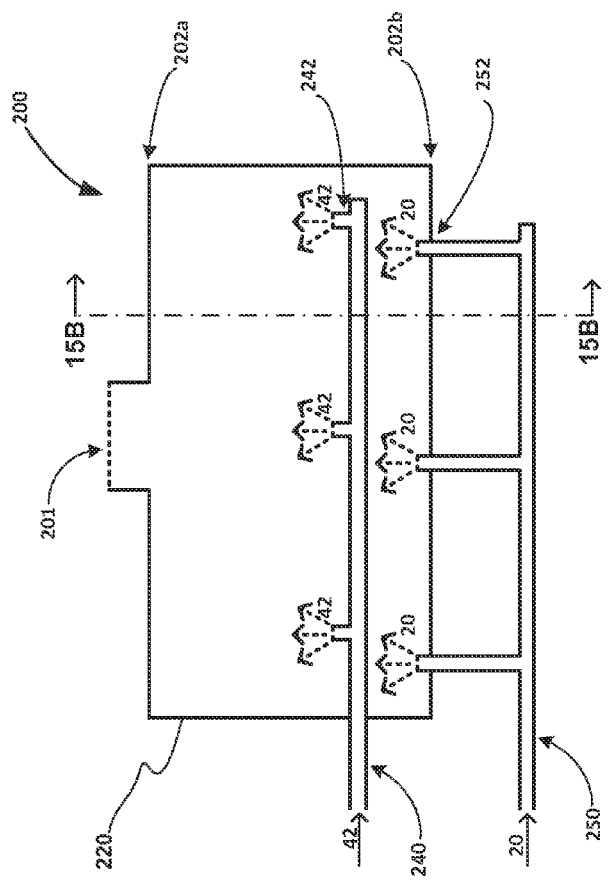
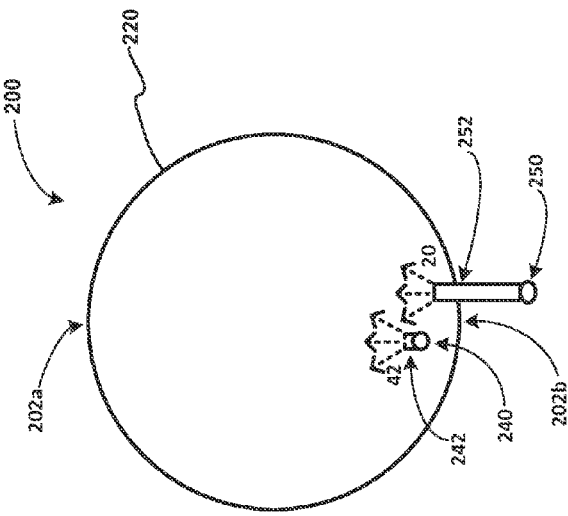

PNEUMATICALLY AGITATED IONIC LIQUID ALKYLATION USING VAPORIZATION TO REMOVE REACTION HEAT

TECHNICAL FIELD

This disclosure relates to systems, reactors, and processes for ionic liquid catalyzed hydrocarbon conversion, such as alkylation, using vaporization to remove reaction heat from the reactor and to provide mixing therein.

BACKGROUND

There is a need for systems, reactors, and processes for ionic liquid catalyzed hydrocarbon conversion, such as alkylation, using vaporization to remove reaction heat from the reactor and to provide mixing therein.

SUMMARY

In an embodiment there is provided a system comprising an ionic liquid reactor configured for performing an ionic liquid catalyzed exothermic hydrocarbon conversion reaction, wherein the ionic liquid reactor comprises a hydrocarbon vapor outlet configured for withdrawing hydrocarbon vapor from the ionic liquid reactor; and the system further comprises: at least one ionic liquid injection nozzle disposed within the ionic liquid reactor, each ionic liquid injection nozzle configured for injecting ionic liquid catalyst into the ionic liquid reactor; at least one hydrocarbon feed injection unit disposed within the ionic liquid reactor, each hydrocarbon feed injection unit configured for injecting a hydrocarbon feed stream into the ionic liquid reactor; a hydrocarbon vapor recovery unit in fluid communication with the hydrocarbon vapor outlet, wherein the hydrocarbon vapor recovery unit is configured for receiving hydrocarbon vapor withdrawn from the ionic liquid reactor and for condensing the withdrawn hydrocarbon vapor to provide a condensed hydrocarbon liquid stream; and a condensed hydrocarbon liquid conduit, in fluid communication with the hydrocarbon vapor recovery unit, configured for recycling the condensed hydrocarbon liquid stream to the ionic liquid reactor.

In another embodiment there is provided a system comprising an ionic liquid reactor configured for performing an ionic liquid catalyzed exothermic hydrocarbon conversion reaction, wherein the ionic liquid reactor comprises at least one hydrocarbon vaporization zone located within the ionic liquid reactor, and a hydrocarbon vapor outlet configured for withdrawing hydrocarbon vapor from the ionic liquid reactor; at least one ionic liquid injection nozzle disposed within the ionic liquid reactor, each ionic liquid injection nozzle configured for injecting ionic liquid catalyst into the ionic liquid reactor; at least one hydrocarbon feed injection unit disposed within the ionic liquid reactor, each hydrocarbon vaporization zone disposed above each hydrocarbon feed injection unit; and a hydrocarbon vapor recovery unit in fluid communication with the hydrocarbon vapor outlet, wherein the hydrocarbon vapor recovery unit is configured for receiving hydrocarbon vapor withdrawn from the ionic liquid reactor and for condensing the withdrawn hydrocarbon vapor to provide a condensed hydrocarbon liquid stream.

In yet another embodiment there is provided a system comprising an ionic liquid reactor configured for performing ionic liquid catalyzed alkylation, wherein the ionic liquid reactor comprises a hydrocarbon vapor outlet configured for withdrawing hydrocarbon vapor from the ionic liquid reactor; and the system further comprises: at least one ionic liquid injection nozzle disposed within the ionic liquid reactor, each ionic liquid injection nozzle configured for injecting an ionic liquid catalyst into the ionic liquid reactor; at least one hydrocarbon feed injection unit disposed within the ionic liquid reactor; a hydrocarbon feed injection conduit, in fluid communication with each hydrocarbon feed injection unit, for feeding a combined feed stream to each hydrocarbon feed injection unit, each hydrocarbon feed injection unit configured for injecting the combined feed stream into the ionic liquid reactor; a hydrocarbon vapor recovery unit in fluid communication with the hydrocarbon vapor outlet, wherein the hydrocarbon vapor recovery unit is configured for receiving hydrocarbon vapor withdrawn from the ionic liquid reactor via the hydrocarbon vapor outlet and for condensing the withdrawn hydrocarbon vapor to provide a condensed hydrocarbon liquid stream; and a condensed hydrocarbon liquid conduit in fluid communication with the hydrocarbon vapor recovery unit and with the hydrocarbon feed injection conduit, wherein the condensed hydrocarbon liquid conduit is configured for feeding the condensed hydrocarbon liquid stream from the hydrocarbon vapor recovery unit to the hydrocarbon feed injection conduit.

In still a further embodiment there is provided a process comprising contacting a hydrocarbon feed stream with an ionic liquid catalyst in an ionic liquid alkylation zone under ionic liquid alkylation conditions to perform an exothermic ionic liquid alkylation reaction; via the heat of reaction of the exothermic alkylation reaction, vaporizing a portion of at least one hydrocarbon in the ionic liquid alkylation zone to provide hydrocarbon vapor in the ionic liquid alkylation zone; withdrawing at least a portion of the hydrocarbon vapor from the ionic liquid alkylation zone; condensing the withdrawn hydrocarbon vapor to provide a condensed hydrocarbon liquid stream; and recycling the condensed hydrocarbon liquid stream to the ionic liquid alkylation zone.

In yet a further embodiment there is provided a process comprising contacting at least one isoparaffin and at least one olefin with an ionic liquid catalyst in an ionic liquid alkylation zone under ionic liquid alkylation conditions to perform an exothermic ionic liquid alkylation reaction, wherein the ionic liquid alkylation zone contains a liquid reaction medium comprising droplets of the ionic liquid catalyst dispersed in a liquid hydrocarbon phase; via the heat of reaction of the exothermic ionic liquid alkylation reaction, vaporizing a portion of at least one hydrocarbon in the ionic liquid alkylation zone to form bubbles of hydrocarbon vapor within the liquid reaction medium; via the bubbles of hydrocarbon vapor, pneumatically agitating the liquid reaction medium in the ionic liquid alkylation zone; withdrawing at least a portion of the hydrocarbon vapor from the ionic liquid alkylation zone; condensing the withdrawn hydrocarbon vapor to provide a condensed hydrocarbon liquid stream; and recycling the condensed hydrocarbon liquid stream to the ionic liquid alkylation zone.

In another embodiment there is provided a process comprising injecting a combined feed stream into an ionic liquid alkylation zone, wherein the combined feed stream comprises at least one $C_4$-$C_{10}$ isoparaffin and at least one $C_2$-$C_{10}$ olefin; injecting an ionic liquid catalyst into the ionic liquid alkylation zone via at least one ionic liquid injection nozzle; contacting the at least one isoparaffin and the at least one olefin with the ionic liquid catalyst in the ionic liquid alkylation zone under ionic liquid alkylation conditions to perform an exothermic ionic liquid alkylation reaction in a liquid reaction medium; via the heat of reaction of the exothermic ionic liquid alkylation reaction, vaporizing a portion of at least one hydrocarbon component of the combined feed stream to provide hydrocarbon vapor in the ionic liquid alkylation zone; withdrawing at least a portion of the hydrocarbon vapor from the ionic liquid alkylation zone, wherein the hydrocarbon vapor comprises a $C_3$-$C_4$ hydrocarbon selected from the group consisting of propane, isobutane, n-butane, and combinations thereof; condensing the withdrawn hydrocarbon vapor to provide a condensed hydrocarbon liquid stream; merging the condensed hydrocarbon liquid stream with an olefin feed stream and an isobutane recycle stream to provide the combined feed stream; withdrawing aliquots of the liquid reaction medium from the ionic liquid alkylation zone to provide a reactor effluent stream; separating the reactor effluent stream into an ionic liquid phase and a hydrocarbon phase; and fractionating the hydrocarbon phase to provide the isobutane recycle stream and an alkylate product.

Further embodiments of systems and processes for ionic liquid catalyzed hydrocarbon conversion are described hereinbelow and shown in the Drawings. As used herein, the terms "comprising" and "comprises" mean the inclusion of named elements or steps that are identified following those terms, but not necessarily excluding other unnamed elements or steps.

BRIEF DESCRIPTION OF THE DRAWINGS

FIG. 9A schematically represents a vertically oriented ionic liquid reactor including a draft tube, and FIG. 9B shows the ionic liquid reactor of FIG. 9A as seen along the line 9B-9B, according to an embodiment of the present invention;

FIG. 9C schematically represents an inner zone and an outer zone within a vertically oriented ionic liquid reactor, and FIG. 9D shows the ionic liquid reactor of FIG. 9C as seen along the line 9D-9D, according to an embodiment of the present invention;

FIG. 10A schematically represents a vertically oriented ionic liquid reactor including a draft tube having an enlarged draft tube upper portion, and FIG. 10B shows the ionic liquid reactor of FIG. 10A as seen along the line 10B-10B, according to an embodiment of the present invention;

FIG. 12A schematically represents an ionic liquid reactor indicating a hydrocarbon vaporization zone in relation to a hydrocarbon feed injection unit, and FIG. 12B shows the ionic liquid reactor of FIG. 12A as seen along the line 12B-12B, according to an embodiment of the present invention;

FIG. 12C schematically represents an ionic liquid reactor indicating a hydrocarbon vaporization zone in relation to each hydrocarbon feed injection unit, according to an embodiment of the present invention;

FIG. 13C schematically represents a basal portion of a vertically oriented ionic liquid reactor having horizontally spaced hydrocarbon feed injection units in an outer zone of the ionic liquid reactor and horizontally spaced ionic liquid injection nozzles in an inner zone of the ionic liquid reactor, according to an embodiment of the present invention;

FIG. 14A schematically represents a horizontally oriented ionic liquid reactor having horizontally spaced hydrocarbon feed injection units and horizontally spaced ionic liquid injection nozzles showing injection of hydrocarbon feed and ionic liquid catalyst in different directions, and FIG. 14B shows the ionic liquid reactor of FIG. 14A as seen along the line 14B-14B, according to an embodiment of the present invention;

FIG. 15A schematically represents a horizontally oriented ionic liquid reactor having horizontally spaced hydrocarbon feed injection units and ionic liquid injection nozzles disposed adjacent to the hydrocarbon feed injection units, and FIG. 15B shows the ionic liquid reactor of FIG. 15A as seen along the line 15B-15B, according to an embodiment of the present invention.

DETAILED DESCRIPTION

Figure 1:
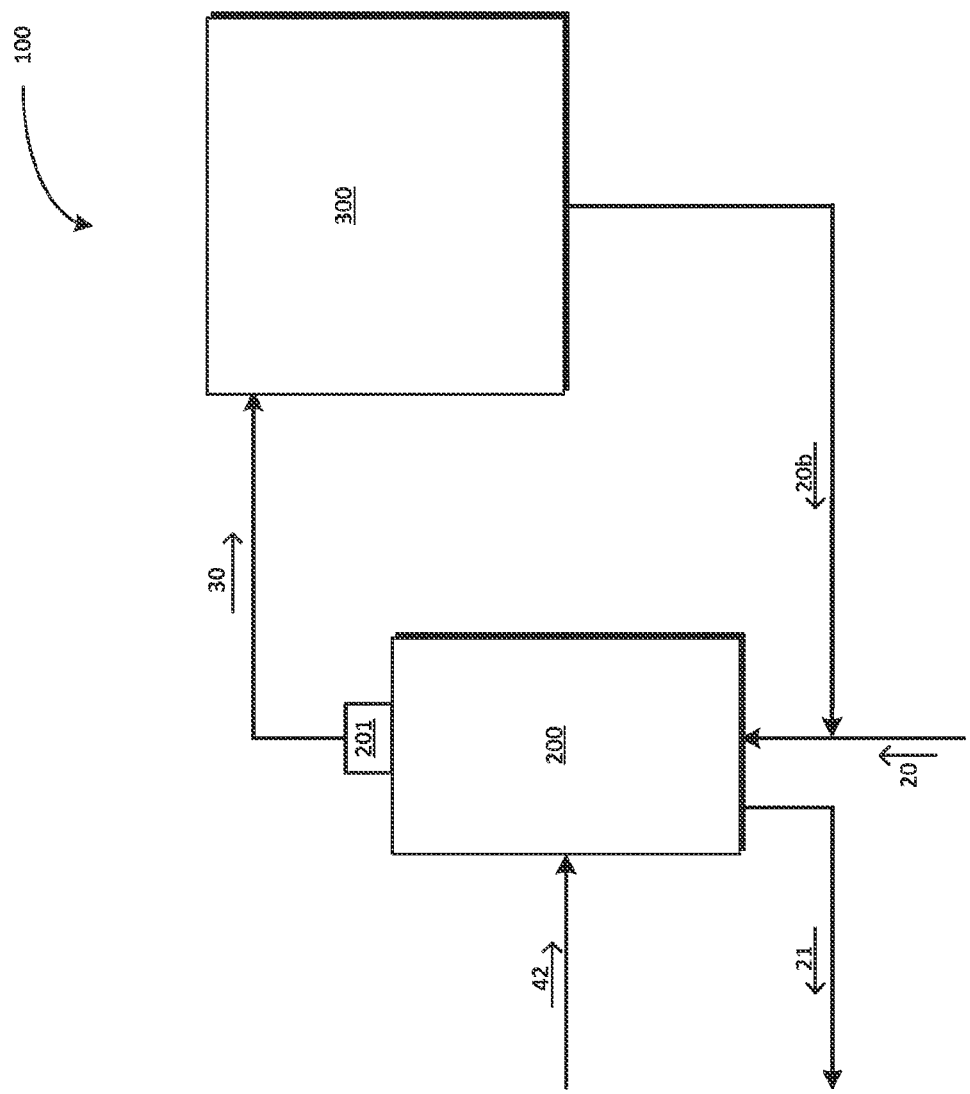
FIG. 1 schematically represents a system and process for ionic liquid catalyzed hydrocarbon conversion including a hydrocarbon vapor recovery unit, according to an embodiment of the present invention.

Ionic liquid catalysts may be useful for hydrocarbon conversion reactions, including alkylation reactions for the production of alkylate gasoline blending components, and the like. Systems for ionic liquid catalyzed hydrocarbon conversion according to this disclosure may comprise an ionic liquid reactor and a hydrocarbon vapor recovery unit, wherein the hydrocarbon vapor recovery unit is in fluid communication with the ionic liquid reactor for recovering hydrocarbon vapor, the ionic liquid reactor may be cooled via hydrocarbon vaporization within the ionic liquid reactor, and the hydrocarbon vapor may be recycled from the hydrocarbon vapor recovery unit to the ionic liquid reactor.

Ionic liquid reactors as disclosed herein also provide for mixing and circulation of liquid reaction medium, comprising ionic liquid catalyst and hydrocarbon reactants, so as to generate a large surface area of ionic liquid catalyst phase in an ionic liquid/hydrocarbon mixture. Such mixing and circulation may be primarily due to the hydrocarbon vaporization causing turbulence within the ionic liquid reactor, e.g., the ionic liquid reactor may be pneumatically agitated via bubbles of hydrocarbon vapor generated within the liquid reaction medium as a result of reaction heat from an exothermic reaction. As a result, the ionic liquid reactor may be operated with no moving parts.

Systems for Ionic Liquid Catalyzed Hydrocarbon Conversion

Systems for ionic liquid catalyzed hydrocarbon conversion processes may comprise an ionic liquid reactor. In an embodiment, the ionic liquid reactor may be configured for performing ionic liquid catalyzed exothermic hydrocarbon conversion reactions, such as alkylation. The ionic liquid reactor may comprise a hydrocarbon vapor outlet configured for withdrawing hydrocarbon vapor from the ionic liquid reactor. In an embodiment, the hydrocarbon vapor outlet may be disposed at the top of the ionic liquid reactor. In a sub-embodiment, the ionic liquid reactor may be vertically oriented and the hydrocarbon vapor outlet may be axially disposed with respect to the ionic liquid reactor. In an embodiment, the ionic liquid reactor may be horizontally oriented.

Such systems may further comprise at least one ionic liquid injection nozzle. In an embodiment, each ionic liquid injection nozzle may be disposed within the ionic liquid reactor. Each ionic liquid injection nozzle may be configured for injecting ionic liquid catalyst into the ionic liquid reactor. In an embodiment, each ionic liquid injection nozzle may comprise any nozzle or opening for providing droplets of ionic liquid catalyst of a suitable size or size range. In an embodiment, each ionic liquid injection nozzle may be configured to produce small to microscopic droplets of ionic liquid catalyst within the ionic liquid reactor. In an embodiment, such droplets of ionic liquid catalyst may have a diameter in the range from 1 to 1000 microns, or from 5 to 500 microns, or from 10 to 250 microns.

Such droplets may provide not only an ionic liquid catalyst surface area that will produce a high rate of reaction and a high quality product (e.g., alkylate), but also a liquid reaction medium (hydrocarbon/ionic liquid mixed phase) that is conducive to subsequent phase separation downstream. The size or size range of ionic liquid droplets produced by the ionic liquid injection nozzles may be selected, for example, by adjusting the flow rate of an ionic liquid feed, or by the number, size, and configuration of the ionic liquid injection nozzles. In an embodiment, an ionic liquid injection nozzle may be in the form of one or more apertures in a conduit or pipe and the like. In an embodiment, each of the ionic liquid injection nozzles may be configured for injecting the ionic liquid catalyst into the ionic liquid reactor in an upward direction or in a downward direction.

Such systems may further comprise at least one hydrocarbon feed injection unit. In an embodiment, each hydrocarbon feed injection unit may be disposed within the ionic liquid reactor. Each hydrocarbon feed injection unit may be configured for injecting a hydrocarbon feed stream into the ionic liquid reactor. In an embodiment, each hydrocarbon feed injection unit may comprise a hydrocarbon feed injection nozzle or a hydrocarbon feed injection sparger. In an embodiment, a feed injection sparger may be considered as an array of hydrocarbon feed injection nozzles. In an embodiment, a hydrocarbon feed injection nozzle may be in the form of one or more apertures (holes, voids, slits, etc.) in a conduit or pipe and the like. In an embodiment, a hydrocarbon injection sparger may be in the form of an array of such apertures in a conduit or pipe and the like. In an embodiment, each hydrocarbon feed injection unit may be configured for injecting the hydrocarbon feed stream into the ionic liquid reactor in an upward direction, or toward the reactor top.

Such systems may still further comprise a hydrocarbon vapor recovery unit in fluid communication with the hydrocarbon vapor outlet. The hydrocarbon vapor recovery unit may be configured for receiving hydrocarbon vapor withdrawn from the ionic liquid reactor and for condensing the withdrawn hydrocarbon vapor to provide a condensed hydrocarbon liquid stream. In an embodiment, the hydrocarbon vapor recovery unit may comprise one or more components selected from a vapor/entrained liquid separator, a gas compressor, a heat exchanger, a gas/condensed liquid separator, and combinations thereof.

In an embodiment, the hydrocarbon vapor recovery unit may be configured for recovering at least 5 mol % of the hydrocarbon feed stream injected into the ionic liquid reactor, or in the range from 5-50 mol % of the hydrocarbon feed stream injected into the ionic liquid reactor. In an embodiment, the hydrocarbon vapor recovery unit may be configured for recovering the hydrocarbon vapor withdrawn from the ionic liquid reactor to provide a condensed hydrocarbon liquid stream, and the system may be configured for recycling the condensed hydrocarbon liquid stream to the ionic liquid reactor. In an embodiment, the condensed hydrocarbon liquid stream may represent at least 5 mol % of the hydrocarbon feed stream injected into the ionic liquid alkylation reactor, or in the range from 5-50 mol % of the hydrocarbon feed stream injected into the ionic liquid reactor.

In an embodiment, the hydrocarbon vapor recovery unit may comprise: a vapor/entrained liquid separator in fluid communication with, and disposed downstream from, the hydrocarbon vapor outlet; a gas compressor in fluid communication with, and disposed downstream from, the vapor/entrained liquid separator; a heat exchanger in fluid communication with, and disposed downstream from, the gas compressor; and a gas/condensed liquid separator in fluid communication with, and disposed downstream from, the heat exchanger.

Such systems may yet further comprise a condensed hydrocarbon liquid conduit in fluid communication with the hydrocarbon vapor recovery unit. In an embodiment, the condensed hydrocarbon liquid conduit may be configured for recycling the condensed hydrocarbon liquid stream to the ionic liquid reactor. In an embodiment, the hydrocarbon vapor recovery unit may be configured for recycling the condensed hydrocarbon liquid stream en masse to the ionic liquid reactor, i.e., the condensed hydrocarbon liquid stream may be recycled to the ionic liquid reactor as a whole without any attempt to separate any constituents of the condensed hydrocarbon liquid stream.

In an embodiment, the ionic liquid reactor may be substantially cylindrical. The ionic liquid reactor may be oriented in an orientation selected from the group consisting of vertically oriented and horizontally oriented. The ionic liquid reactor may have a reactor base, a reactor top, and a reactor effluent outlet. In an embodiment, the reactor effluent outlet may be disposed at the reactor base, and the hydrocarbon vapor outlet may be disposed at the reactor top. In an embodiment, each of a plurality of the ionic liquid injection nozzles may be disposed at substantially the same height from the reactor base.

In an embodiment, each ionic liquid injection nozzle may be disposed in a lower or basal portion of the ionic liquid reactor, and each ionic liquid injection nozzle may be configured for injecting the ionic liquid catalyst into the ionic liquid reactor in an upward direction. In another embodiment, each ionic liquid injection nozzle may be disposed in an upper or top portion of the ionic liquid reactor, and each ionic liquid injection nozzle may be configured for injecting the ionic liquid catalyst into the ionic liquid reactor in a downward direction. By the expression, "top portion" as used herein is meant a portion of the ionic liquid reactor at, near, or toward the top of the ionic liquid reactor.

In a further embodiment, each hydrocarbon feed injection unit may be disposed in a lower or basal portion of the ionic liquid reactor, and each hydrocarbon feed injection unit may be configured for injecting the hydrocarbon feed stream into the ionic liquid reactor in an upward direction. In an embodiment, each ionic liquid injection nozzle may be disposed adjacent to each hydrocarbon feed injection unit. In an embodiment, the at least one hydrocarbon feed injection unit may comprise a plurality of hydrocarbon feed injection units, and the plurality of hydrocarbon feed injection units may be spaced apart from each other in a manner selected from horizontally spaced apart, vertically spaced apart, and combinations thereof. That is to say, a plurality of hydrocarbon feed injection units disposed within the ionic liquid reactor may be spaced apart from each other horizontally, vertically, or both horizontally and vertically.

In an embodiment, the ionic liquid reactor may comprise a substantially cylindrical reactor wall. In a sub-embodiment, the ionic liquid reactor may be vertically oriented, and a draft tube may be disposed within the ionic liquid reactor. In an embodiment, the draft tube may be disposed coaxially within the reactor wall. The draft tube may define an inner zone within the draft tube, and the reactor wall and draft tube may jointly define an outer zone external to the draft tube.

In an embodiment, the draft tube may be shorter than the reactor wall such that the reactor wall may extend above the top of the draft tube and/or below the bottom of the draft tube. For the purpose of describing the location of the hydrocarbon feed units and ionic liquid injection nozzles, however, the inner zone may be considered to extend above and/or below the ends of the draft tube, e.g., over the entire length (or height) of the ionic liquid reactor. In this disclosure, the concept of an inner zone and an outer zone of a vertically oriented, cylindrical ionic liquid reactor may also be applied to embodiments that lack a draft tube per se.

In an embodiment, at least one hydrocarbon feed injection unit may be disposed within the inner zone. In a sub-embodiment, at least one hydrocarbon feed injection unit may be coaxial with the inner zone. In another embodiment, at least one hydrocarbon feed injection unit may be disposed in the outer zone, i.e., external to the draft tube.

In an embodiment, the ionic liquid reactor may be vertically oriented, at least one hydrocarbon feed injection unit may be disposed axially with respect to the ionic liquid reactor, and the at least one hydrocarbon feed injection unit may be configured for injecting the hydrocarbon feed stream in an upward direction into the inner zone of the ionic liquid reactor.

In another embodiment, the ionic liquid reactor may be vertically oriented, and the system may further comprise a draft tube disposed vertically within the ionic liquid reactor to define the inner zone within the draft tube and the outer zone external to the draft tube, wherein at least one ionic liquid injection nozzle may be disposed in the outer zone and at least one hydrocarbon feed injection unit may be disposed in the inner zone.

In a further embodiment, the ionic liquid reactor may be vertically oriented, and the system may further comprise a draft tube disposed vertically within the ionic liquid reactor to define the inner zone within the draft tube and the outer zone external to the draft tube, wherein at least one ionic liquid injection nozzle and at least one hydrocarbon feed injection unit may be disposed in the inner zone.

In yet another embodiment, the ionic liquid reactor may be vertically oriented, and the system may further comprise a draft tube disposed vertically within the ionic liquid reactor to define the inner zone within the draft tube and the outer zone external to the draft tube, wherein at least one ionic liquid injection nozzle and at least one hydrocarbon feed injection unit may be disposed in the outer zone.

In an embodiment, the ionic liquid reactor may have a draft tube disposed vertically therein, wherein the draft tube may include an expanded or enlarged upper portion. As an example, the draft tube may have a larger diameter at the draft tube upper portion than at a lower portion of the draft tube (see, for example, FIGS. 10A-10B). In an embodiment, the draft tube lower portion may be cylindrical, and the draft tube upper portion may have a tapered wall. In a sub-embodiment, the draft tube may have a frusto-conical upper portion. While not being bound by theory, the enlarged upper portion of the draft tube may promote vapor bubble disengagement from the liquid reaction medium in an upper portion of the ionic liquid reactor so as to enhance hydrocarbon vapor-liquid phase separation and facilitate the separate withdrawal of hydrocarbon vapor from the top of the ionic liquid reactor, i.e., such that the hydrocarbon vapor may be withdrawn in the substantial absence of liquid reaction medium.

In an embodiment, the system may further comprise a demister unit in fluid communication with the hydrocarbon vapor outlet of the ionic liquid reactor. In an embodiment, the demister unit may be configured for removing entrained liquid (e.g., ionic liquid droplets) from the hydrocarbon vapor. In an embodiment, the demister unit may be disposed upstream from the hydrocarbon vapor recovery unit. In an embodiment, the demister unit may be integral with the ionic liquid reactor. In a sub-embodiment, the demister unit may be disposed within a neck of the ionic liquid reactor disposed at or near the top of the ionic liquid reactor. In an embodiment, the demister unit may include demist packing material. In an embodiment, ionic liquid droplets entrained by a hydrocarbon vapor stream from the hydrocarbon vapor outlet may coalesce in the demister unit, and such coalesced ionic liquid may be returned to the ionic liquid reactor.

In an embodiment, the ionic liquid reactor may comprise a reactor effluent outlet configured for withdrawing liquid reaction medium from the ionic liquid reactor, e.g., to provide a reactor effluent stream. In a sub-embodiment, the ionic liquid reactor may be vertically oriented. In an embodiment, the reactor effluent outlet may be disposed at a lower or basal portion of the ionic liquid reactor, e.g., in the reactor base. In another embodiment, the reactor effluent outlet may be disposed laterally at the side of the ionic liquid reactor. In a sub-embodiment, the level of liquid reaction medium in the ionic liquid reactor may be controlled via "overflow" from the lateral reactor effluent outlet. In another embodiment, the level of liquid reaction medium in the ionic liquid reactor may be controlled via an effluent control valve in combination with a level gauge for monitoring the level in the ionic liquid reactor and for signaling the effluent control valve.

In an embodiment, the ionic liquid reactor may lack a gas phase feed or inlet. In an embodiment, the ionic liquid reactor may provide sufficient turbulence and mixing of the ionic liquid catalyst droplets and liquid hydrocarbons to efficiently perform alkylation in the absence of any moving parts within the ionic liquid reactor other than fluid flow. In an embodiment, the circulation or flow of liquid reaction medium within the ionic liquid reactor may be driven, in part, by the vaporization of hydrocarbons within the ionic liquid reactor due to the generation of heat (heat of reaction) from exothermic hydrocarbon conversion, e.g., alkylation, reactions.

In an embodiment, sources of mixing within the ionic liquid reactor may include injecting the hydrocarbon feed into the ionic liquid reactor and injecting the ionic liquid catalyst into the ionic liquid reactor. These sources of mixing may be more pronounced when the hydrocarbon feed stream and ionic liquid catalyst are injected countercurrent. In an embodiment, higher rates of mixing may be generated by i) local turbulence, e.g., above or adjacent to each hydrocarbon feed injection unit due to enhanced vaporization of hydrocarbons in the liquid reaction medium, and ii) circulation of the liquid reaction medium within the ionic liquid reactor, e.g., the liquid reaction medium may flow in a first direction in the inner zone and in the opposite direction in the outer zone of the ionic liquid reactor. As a non-limiting example, the flow of the liquid reaction medium may be upward in the inner zone and downward in the outer zone, or vice versa (see, e.g., FIGS. 13A-13C).

In an embodiment, the ionic liquid reactor may be configured for containing a liquid reaction medium, and mixing of the liquid reaction medium may occur primarily due to hydrocarbon vaporization in the reactor and in the absence of any moving parts. As an example, the ionic liquid reactor may be pneumatically agitated by bubbles of hydrocarbon vapor generated within the liquid reaction medium via reaction heat from an exothermic hydrocarbon conversion reaction. At least a portion of the hydrocarbon vapor may rise in the reactor and provide agitation and mixing of the reactor contents. Such a reactor may be referred to herein as a pneumatically agitated ionic liquid reactor.

In an embodiment, the hydrocarbon feed stream may be injected, via a hydrocarbon feed injection unit, into or toward a region of enhanced hydrocarbon vaporization, as compared with the rate of hydrocarbon vaporization for the ionic liquid reactor as a whole. Such a region of enhanced hydrocarbon vaporization may be referred to herein as a hydrocarbon vaporization zone. While not being bound by theory, enhanced hydrocarbon vaporization in the hydrocarbon vaporization zone may be due to a higher rate of ionic liquid alkylation reaction in the proximity of hydrocarbon feed injection.

In an embodiment, a hydrocarbon feed stream may be injected in an upward direction from at least one hydrocarbon feed injection unit into the ionic liquid reactor, such that a hydrocarbon vaporization zone may be located above each hydrocarbon feed injection unit. In an embodiment, each hydrocarbon feed injection unit may be located in a lower or basal portion of the ionic liquid reactor. In an embodiment, the liquid reaction medium may circulate within the ionic liquid reactor in a defined manner. In an embodiment, such circulation of the liquid reaction medium within the ionic liquid reactor may be driven primarily by hydrocarbon vaporization in the one or more hydrocarbon vaporization zones.

In an embodiment, the ionic liquid reactor may further comprise a liquid recycle outlet disposed at the basal portion of the ionic liquid reactor. In a sub-embodiment, the liquid recycle outlet may be located at the base of the ionic liquid reactor. The liquid recycle outlet may be configured for withdrawing liquid reaction medium from the basal portion of the ionic liquid reactor. The liquid recycle outlet may be in fluid communication with each ionic liquid injection nozzle for injecting the recycled liquid reaction medium into the ionic liquid reactor. By the expression, "basal portion" as used herein is meant a portion of the ionic liquid reactor at, near, or toward the base of the ionic liquid reactor.

According to another embodiment of a system for ionic liquid catalyzed hydrocarbon conversion, the system may comprise an ionic liquid reactor configured for performing ionic liquid catalyzed hydrocarbon conversion reactions. The ionic liquid reactor may comprise at least one hydrocarbon vaporization zone located therein, and a hydrocarbon vapor outlet configured for withdrawing hydrocarbon vapor from the ionic liquid reactor.

The system may further comprise at least one ionic liquid injection nozzle disposed within the ionic liquid reactor. Each ionic liquid injection nozzle may be configured for injecting ionic liquid catalyst into the ionic liquid reactor. The system may still further comprise at least one hydrocarbon feed injection unit disposed within the ionic liquid reactor. In an embodiment, a hydrocarbon vaporization zone may be disposed above each hydrocarbon feed injection unit. In an embodiment, the system may be configured for injecting a combined feed stream into the ionic liquid reactor. In a sub-embodiment, the combined feed stream may be injected into the ionic liquid reactor in an upward direction via the hydrocarbon feed injection unit(s). In an embodiment, the combined feed stream may comprise the condensed hydrocarbon liquid stream in combination with at least one of an olefin feed stream, an isoparaffin feed stream, and an isobutane recycle stream.

In an embodiment, the ionic liquid reactor may be pneumatically agitated by bubbles of hydrocarbon vapor generated within each hydrocarbon vaporization zone via reaction heat from an exothermic hydrocarbon conversion reaction. Each hydrocarbon vaporization zone may be characterized as having an enhanced level of hydrocarbon vaporization, as compared with the ionic liquid reactor as a whole (see, for example, FIGS. 12A-12C).

The system may yet further comprise a hydrocarbon vapor recovery unit in fluid communication with the hydrocarbon vapor outlet. The hydrocarbon vapor recovery unit may be configured for receiving hydrocarbon vapor withdrawn from the ionic liquid reactor and for condensing the withdrawn hydrocarbon vapor to provide a condensed hydrocarbon liquid stream. In an embodiment, the hydrocarbon vapor recovery unit may comprise a vapor/entrained liquid separator in fluid communication with the hydrocarbon vapor outlet for separating entrained liquid from the withdrawn hydrocarbon vapor. The hydrocarbon vapor recovery unit may further comprise a gas compressor in fluid communication with the vapor/entrained liquid separator for compressing the withdrawn hydrocarbon vapor. The hydrocarbon vapor recovery unit may still further comprise a heat exchanger in fluid communication with the gas compressor for cooling compressed hydrocarbon vapor. The hydrocarbon vapor recovery unit may further comprise a gas/condensed liquid separator in fluid communication with the heat exchanger for separating non-condensable gases from a condensed hydrocarbon liquid stream.

In an embodiment, the system may further comprise a hydrocarbon feed injection conduit, in fluid communication with each hydrocarbon feed injection unit, for feeding the combined feed stream to each hydrocarbon feed injection unit. In an embodiment, the system may further comprise a condensed hydrocarbon liquid conduit, in fluid communication with the hydrocarbon feed injection conduit and with the gas/condensed liquid separator, for feeding the condensed hydrocarbon liquid stream to the hydrocarbon feed injection conduit.

According to a further embodiment of a system for ionic liquid catalyzed hydrocarbon conversion, the system may comprise an ionic liquid reactor configured for performing ionic liquid catalyzed alkylation. The ionic liquid reactor may comprise a hydrocarbon vapor outlet configured for withdrawing hydrocarbon vapor from the ionic liquid reactor. At least one ionic liquid injection nozzle may be disposed within the ionic liquid reactor, and each ionic liquid injection nozzle may be configured for injecting an ionic liquid catalyst into the ionic liquid reactor. At least one hydrocarbon feed injection unit may also be disposed within the ionic liquid reactor.

The ionic liquid reactor may contain a liquid reaction medium, and the ionic liquid catalyzed alkylation may comprise an exothermic reaction that generates reaction heat sufficient to vaporize some hydrocarbon components of the liquid reaction medium. In an embodiment, the ionic liquid reactor may be pneumatically agitated by bubbles of hydrocarbon vapor generated within the liquid reaction medium via reaction heat from the exothermic alkylation reaction.

The system may further comprise a hydrocarbon vapor recovery unit in fluid communication with the hydrocarbon vapor outlet, wherein the hydrocarbon vapor recovery unit may be configured for receiving hydrocarbon vapor withdrawn from the ionic liquid reactor via the hydrocarbon vapor outlet and for condensing the withdrawn hydrocarbon vapor to provide a condensed hydrocarbon liquid stream. The system may further comprise a hydrocarbon feed injection conduit, in fluid communication with each hydrocarbon feed injection unit, for feeding a combined feed stream to each hydrocarbon feed injection unit. Each hydrocarbon feed injection unit may be configured for injecting the combined feed stream into the ionic liquid reactor.

The system may still further comprise a condensed hydrocarbon liquid conduit in fluid communication with the hydrocarbon vapor recovery unit and with the hydrocarbon feed injection conduit, wherein the condensed hydrocarbon liquid conduit may be configured for feeding the condensed hydrocarbon liquid stream from the hydrocarbon vapor recovery unit to the hydrocarbon feed injection conduit. In an embodiment, the combined feed stream may comprise the condensed hydrocarbon liquid stream and an olefin feed stream. In an embodiment, the combined feed stream may further comprise an isobutane recycle stream. In an embodiment, the combined feed stream may still further comprise an isoparaffin feed stream.

The system may yet further comprise a demister unit in fluid communication with the hydrocarbon vapor outlet. In an embodiment, the demister unit may be configured for removing entrained droplets of ionic liquid from the withdrawn hydrocarbon vapor. The hydrocarbon vapor recovery unit may comprise a vapor/entrained liquid separator in fluid communication with, and disposed downstream from, the demister unit. In an embodiment, the vapor/entrained liquid separator may be configured for separating any residual entrained liquid from the withdrawn hydrocarbon vapor. The hydrocarbon vapor recovery unit may further comprise a gas compressor in fluid communication with, and disposed downstream from, the vapor/entrained liquid separator, wherein the gas compressor may be configured for compressing the withdrawn hydrocarbon vapor.

The hydrocarbon vapor recovery unit may still further comprise a heat exchanger in fluid communication with, and disposed downstream from, the gas compressor, wherein the heat exchanger may be configured for cooling the compressed hydrocarbon vapor. The hydrocarbon vapor recovery unit may yet further comprise a gas/condensed liquid separator in fluid communication with, and disposed downstream from, the heat exchanger, wherein the gas/condensed liquid separator may be configured for separating non-condensable gases from the condensed hydrocarbon liquid stream.

Ionic Liquid Catalyzed Hydrocarbon Conversion Processes

According to another embodiment, a process for ionic liquid catalyzed hydrocarbon conversion, e.g., isoparaffin/olefin alkylation, may be practiced using systems comprising an ionic liquid reactor as disclosed herein comprising an ionic liquid alkylation zone. Systems for such ionic liquid catalyzed processes may further comprise additional elements, features, and characteristics as described herein and as shown in the drawings.

In an embodiment, a process for ionic liquid catalyzed alkylation may include contacting a hydrocarbon feed stream with an ionic liquid catalyst in an ionic liquid alkylation zone under ionic liquid alkylation conditions to perform an exothermic ionic liquid alkylation reaction. In an embodiment, such process may further include vaporizing a portion of at least one hydrocarbon in the ionic liquid alkylation zone to provide hydrocarbon vapor in the ionic liquid alkylation zone. Such hydrocarbon vaporization may be induced via the heat of reaction of the exothermic ionic liquid alkylation reaction. In an embodiment, the at least one hydrocarbon may be a component of the hydrocarbon feed stream. In an embodiment, the at least one hydrocarbon may comprise a $C_3$-$C_4$ hydrocarbon. In a sub-embodiment, the at least one hydrocarbon vaporized in the ionic liquid alkylation zone may be selected from propane, n-butane, isobutane, and combinations thereof.

In an embodiment, heat may be removed from the ionic liquid alkylation zone via said hydrocarbon vaporization, e.g., so as to offset the heat of reaction generated within the ionic liquid alkylation zone. In a sub-embodiment, the heat removed by hydrocarbon vaporization in the ionic liquid alkylation zone may be substantially equivalent to the heat of reaction generated by the exothermic reaction(s) in the ionic liquid alkylation zone.

In an embodiment, such process for ionic liquid catalyzed alkylation may further include withdrawing at least a portion of the hydrocarbon vapor from the ionic liquid alkylation zone. In an embodiment, withdrawing the hydrocarbon vapor from the ionic liquid alkylation zone may comprise withdrawing all, or substantially all, of the hydrocarbon vapor that rises to the top of the ionic liquid alkylation zone. The ionic liquid alkylation zone may contain a liquid reaction medium in addition to the hydrocarbon vapor. In an embodiment, the hydrocarbon vapor may be withdrawn, e.g., via a hydrocarbon vapor outlet, from a top portion of the ionic liquid alkylation zone in the substantial absence of liquid reaction medium. By the expression, "top portion" as used herein is meant a portion of the ionic liquid alkylation zone at, near, or toward the top of the ionic liquid alkylation zone.

The process may further include condensing the withdrawn hydrocarbon vapor to provide a condensed hydrocarbon liquid stream. In an embodiment, the withdrawn hydrocarbon vapor may be condensed by cooling the withdrawn hydrocarbon vapor, by compressing the withdrawn hydrocarbon vapor, or by a combination thereof. In a sub-embodiment, the condensed hydrocarbon liquid stream may be provided by compressing the withdrawn hydrocarbon vapor and thereafter cooling the compressed hydrocarbon vapor. In an embodiment, a gas compressor for compressing the withdrawn hydrocarbon vapor may comprise carbon steel. The process may still further include recycling the condensed hydrocarbon liquid stream to the ionic liquid alkylation zone.

Prior to the condensing step, any entrained droplets of ionic liquid may be removed from the withdrawn hydrocarbon vapor. In an embodiment, such entrained droplets of ionic liquid may be removed from the hydrocarbon vapor by passing the hydrocarbon vapor through a demister unit. In an embodiment, the demister unit may include or contain a demist packing material. In an embodiment, droplets of ionic liquid may coalesce on the demist packing material of the demister unit, and such droplets may be returned to the ionic liquid alkylation zone, e.g., via gravity. In an embodiment, any residual entrained droplets of ionic liquid may also be removed from the hydrocarbon vapor via a vapor/entrained liquid separator disposed downstream from the demister unit.

In an embodiment, the withdrawn hydrocarbon vapor may be cooled via a heat exchanger, and the process may further comprise, optionally, adjusting coolant flow rate to the heat exchanger so as to control the temperature of the ionic liquid alkylation zone. Adjusting coolant flow rate to the heat exchanger is a non-limiting example of optionally providing additional cooling, i.e., in addition to that provided by hydrocarbon vaporization, to the ionic liquid alkylation zone. In an embodiment, the heat exchanger may comprise a shell and tube heat exchanger. In a sub-embodiment the heat exchanger may comprise carbon steel.

In an embodiment, non-condensable gases may be separated from the condensed hydrocarbon liquid stream prior to recycling the condensed hydrocarbon liquid stream to the ionic liquid alkylation zone. In an embodiment, the non-condensable gases may be separated from the condensed hydrocarbon liquid stream via a gas/condensed liquid separator. In an embodiment, the condensed hydrocarbon liquid stream may comprise at least one $C_3$-$C_4$ alkane.

In an embodiment, the hydrocarbon vapor withdrawn from the ionic liquid reactor may comprise propane, and the step of recycling the condensed hydrocarbon liquid stream may comprise recycling the propane to the ionic liquid alkylation zone via (i.e., as a component of) the condensed hydrocarbon liquid stream. In an embodiment, at least 50%, or at least 75%, or at least 90%, or at least 95%, or at least 99% of the propane present in the withdrawn hydrocarbon vapor may be recycled to the ionic liquid alkylation zone via the condensed hydrocarbon liquid stream. In an embodiment, the step of recycling the condensed hydrocarbon liquid stream may comprise recycling the condensed hydrocarbon liquid stream to the ionic liquid alkylation zone without any fractionation of the condensed hydrocarbon liquid stream, i.e., by recycling the condensed hydrocarbon liquid stream to the ionic liquid alkylation zone en masse.

In an embodiment, the ionic liquid alkylation zone may contain a liquid reaction medium comprising droplets of the ionic liquid catalyst dispersed in a liquid hydrocarbon phase. The step of vaporizing at least one hydrocarbon may comprise forming bubbles of hydrocarbon vapor within the liquid reaction medium, and the process may further comprise pneumatically agitating the liquid reaction medium via the bubbles of hydrocarbon vapor. At least a portion of the bubbles of hydrocarbon vapor may rise through the liquid reaction medium to a top portion of the ionic liquid alkylation zone, where the bubbles of hydrocarbon vapor may disengage from the liquid reaction medium. Mixing of a liquid reaction medium contained in the ionic liquid alkylation zone resulting from hydrocarbon vaporization, e.g., due to turbulence, may be referred to herein as pneumatic agitation.

In an embodiment, the ionic liquid alkylation zone may be held substantially at constant temperature and constant pressure. As a non-limiting example, the ionic liquid alkylation zone temperature may be held at ±5° F. of a target temperature value, and the ionic liquid alkylation zone pressure may be held at ±35 kPa of a target pressure value. In an embodiment, there is no gas phase inlet to the ionic liquid alkylation zone and no gas phase feed during the ionic liquid alkylation process.

In an embodiment, the hydrocarbon feed stream to the ionic liquid alkylation zone may comprise a combined feed stream. In an embodiment, the combined feed stream may comprise at least one olefin and at least one isoparaffin. In an embodiment, the step of recycling the condensed hydrocarbon liquid stream to the ionic liquid alkylation zone may comprise merging the condensed hydrocarbon liquid stream with an olefin feed stream and an isobutane recycle stream to provide the combined feed stream.

In an embodiment, the ionic liquid alkylation process conditions may be selected for vaporizing a portion of a liquid hydrocarbon in the ionic liquid reactor sufficient to remove at least a portion of the heat generated during the exothermic ionic liquid alkylation reaction, such that any extraneous cooling of the ionic liquid alkylation zone (reactor) may be unnecessary, minimized, or decreased.

In an embodiment, the exothermic ionic liquid alkylation reaction may occur in the liquid phase, the combined feed stream may comprise at least one $C_3$-$C_4$ alkane, and the ionic liquid alkylation conditions may be selected to promote vaporization of the at least one $C_3$-$C_4$ alkane only in the presence of the exothermic ionic liquid alkylation reaction. In a sub-embodiment, the alkylation conditions may be selected such that $C_3$-$C_4$ vaporization sufficient to provide substantial cooling of the ionic liquid alkylation zone, and/or sufficient to cause substantial turbulence within the ionic liquid alkylation zone, may only occur when the alkylation reaction occurs at or above a threshold rate.

In an embodiment, the process may further comprise injecting the combined feed stream, via at least one hydrocarbon feed injection unit, in an upward direction into the ionic liquid alkylation zone. In an embodiment, the combined feed stream may be injected at, or adjacent to, a location at which hydrocarbon vaporization is enhanced, as compared with the rate of hydrocarbon vaporization for the ionic liquid alkylation zone as a whole. Such a region of enhanced hydrocarbon vaporization may be referred to herein as a hydrocarbon vaporization zone. While not being bound by theory, enhanced hydrocarbon vaporization in the hydrocarbon vaporization zone may be due to a higher rate of ionic liquid alkylation reaction in the proximity of hydrocarbon feed injection. In an embodiment, a hydrocarbon vaporization zone may be located above, and/or adjacent to, each hydrocarbon feed injection unit.

Each feed injection unit may comprise a nozzle or a sparger and the like. In an embodiment, a hydrocarbon injection nozzle may be in the form of one or more apertures, holes, or slits, and the like in a conduit or pipe or the like. In an embodiment, a hydrocarbon injection sparger may be in the form of an array of apertures in a conduit or pipe and the like. In an embodiment, each hydrocarbon feed injection unit may be located in a lower or basal portion of the ionic liquid alkylation zone. In an embodiment, the ionic liquid alkylation zone may contain a liquid reaction medium comprising a liquid hydrocarbon continuous phase and an ionic liquid dispersed phase. By the expression, "basal portion" as used herein is meant a portion of the ionic liquid alkylation zone at, near, or toward the base of the ionic liquid alkylation zone.

In an embodiment, injection of the ionic liquid catalyst may provide small to microscopic ionic liquid catalyst droplets, e.g., having a droplet diameter in the range from 1 to 1000 microns, or from 5 to 500 microns, or from 10 to 250 microns. The ionic liquid injection nozzle(s) may be disposed above-, at-, or below the level of the liquid reaction medium in the ionic liquid alkylation zone. In a sub-embodiment, the ionic liquid injection nozzles may be disposed both above and below the level of the liquid reaction medium in the ionic liquid alkylation zone. In an embodiment, the liquid reaction medium in the ionic liquid alkylation zone may be maintained at a constant level, e.g., via a level control valve or via "overflow" from a lateral effluent outlet.

In an embodiment, the hydrocarbon vapor withdrawn from the ionic liquid alkylation zone may be equal to at least 5 mol %, or in the range from 5-50 mol %, of a combined feed stream injected into the ionic liquid alkylation zone. In contrast to conventional alkylation, in ionic liquid catalyzed isoparaffin-olefin alkylation for alkylate production hydrocarbons will typically form the continuous phase and represent the vast majority of the reactor contents with only a minor amount of ionic liquid catalyst droplets as the dispersed phase. As a result of the larger relative amount of hydrocarbons in ionic liquid catalyzed alkylation processes much more hydrocarbon vaporization is possible per unit volume of reactor, as compared with conventional alkylation processes (in which a relatively small amount of hydrocarbon is dispersed in a much larger volume of conventional catalyst). In an embodiment, at least 5 mol %, or in the range from 5-50 mol %, of the total hydrocarbon components of the combined feed stream may be vaporized in, withdrawn from, and recycled to, the ionic liquid alkylation zone. In an embodiment, the step of recycling the condensed hydrocarbon liquid stream to the ionic liquid reactor may advantageously increase the isoparaffin/olefin (I/O) ratio in the ionic liquid alkylation zone by at least 5%, or in the range from 5-50%.

During ionic liquid catalyzed alkylation processes as disclosed herein, the ionic liquid alkylation zone may contain a liquid reaction medium comprising droplets of the ionic liquid catalyst dispersed in a liquid hydrocarbon phase. In an embodiment, vaporization of at least one hydrocarbon in the ionic liquid alkylation zone may cause upward flow of the liquid reaction medium, e.g., at a location above each hydrocarbon feed injection unit. In an embodiment, there are no moving parts within the ionic liquid alkylation zone, other than fluid flow.

In an embodiment, a draft tube may be disposed within the ionic liquid alkylation zone to define an inner zone within the draft tube and an outer zone external to the draft tube, wherein the draft tube and the outer zone each contain the liquid reaction medium. In an embodiment, the combined feed stream may be injected into the draft tube, the liquid reaction medium may flow generally upward within the draft tube, and the liquid reaction medium may flow generally downward in the outer zone. In an embodiment, the combined feed stream may be injected axially, in an upward direction, i.e., from substantially the center of the draft tube.

In another embodiment, the combined feed stream may be injected into the outer zone external to the draft tube, the liquid reaction medium may flow generally upward in the outer zone, and the liquid reaction medium may flow generally downward within the draft tube.

In an embodiment, the process may further comprise injecting the ionic liquid catalyst into an outer zone of the ionic liquid alkylation zone via at least one ionic liquid injection nozzle. In an embodiment, the ionic liquid injection nozzles may be located in a top portion of the ionic liquid alkylation zone or in a basal portion of the ionic liquid alkylation zone. The ionic liquid catalyst may be injected into the ionic liquid alkylation zone in an upward direction or in a downward direction.

Figure 13A:
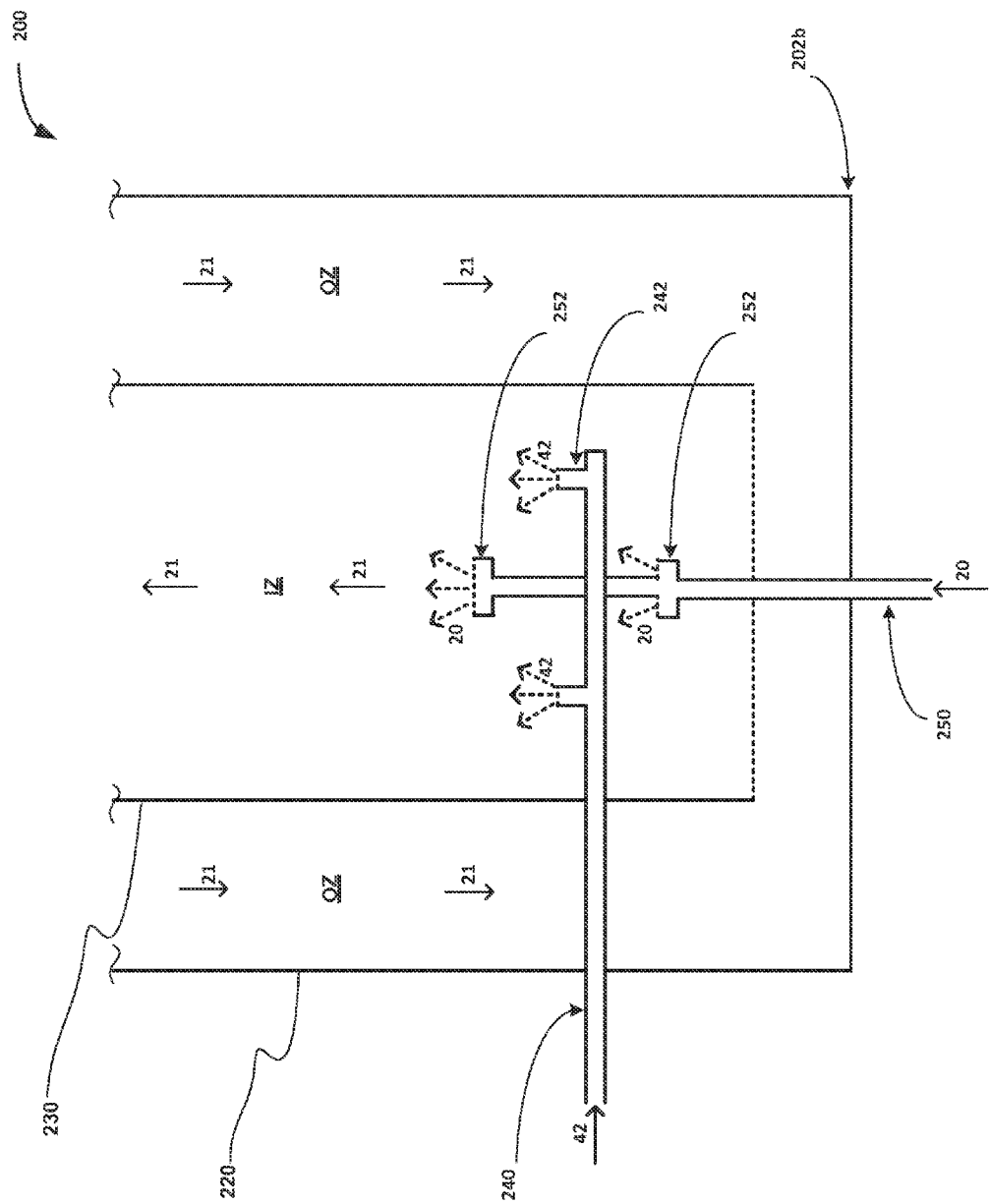
FIG. 13A schematically represents a basal portion of a vertically oriented ionic liquid reactor having vertically spaced hydrocarbon feed injection units and horizontally spaced ionic liquid injection nozzles disposed in an inner zone of the ionic liquid reactor, according to an embodiment of the present invention.

In an embodiment, the process may further comprise injecting the ionic liquid catalyst into an inner zone of the ionic liquid alkylation zone via at least one ionic liquid injection nozzle (see, e.g., FIG. 13A). In another embodiment, the process may further comprise injecting the ionic liquid catalyst into an outer zone of the ionic liquid alkylation zone via at least one ionic liquid injection nozzle (see, e.g., FIG. 13B).

In an embodiment, the process may further comprise withdrawing a liquid reaction medium from a lower or basal portion of the ionic liquid alkylation zone, wherein the liquid reaction medium may comprise the ionic liquid catalyst. In an embodiment, liquid reaction medium may be withdrawn via a liquid recycle outlet located at the base of the ionic liquid alkylation zone. In an embodiment, liquid reaction medium withdrawn from the basal portion of the ionic liquid alkylation zone may be somewhat enriched in ionic liquid catalyst, e.g., due to some settling of coalesced ionic liquid droplets. In an embodiment, the withdrawn liquid reaction medium may be recycled to the ionic liquid alkylation zone via a plurality of ionic liquid injection nozzles. In an embodiment, recycled liquid reaction medium may be combined with recovered and/or makeup ionic liquid catalyst prior to injection into the ionic liquid alkylation zone via the ionic liquid injection nozzle(s).

According to another embodiment, a process for ionic liquid catalyzed alkylation may comprise contacting at least one isoparaffin and at least one olefin with an ionic liquid catalyst in an ionic liquid alkylation zone under ionic liquid alkylation conditions to perform an exothermic ionic liquid alkylation reaction. The ionic liquid alkylation zone may contain a liquid reaction medium comprising droplets of the ionic liquid catalyst dispersed in a liquid hydrocarbon phase. In an embodiment, the exothermic ionic liquid alkylation reaction may be performed in the liquid phase and under conditions below the boiling point of at least one hydrocarbon, wherein the at least one hydrocarbon may be subject to substantial vaporization in one or more regions of the ionic liquid alkylation zone that experience higher rates of the alkylation reaction as compared with the ionic liquid alkylation zone as a whole.

Such process may further comprise vaporizing a portion of the least one hydrocarbon in the ionic liquid alkylation zone to form bubbles of hydrocarbon vapor within the liquid reaction medium. Such process may further comprise pneumatically agitating, via the bubbles of hydrocarbon vapor, the liquid reaction medium in the ionic liquid alkylation zone. In an embodiment, such hydrocarbon vaporization may be induced via the heat of reaction of the exothermic ionic liquid alkylation reaction. In an embodiment, at least a portion of the bubbles of hydrocarbon vapor may rise through the liquid reaction medium to a top portion of the ionic liquid alkylation zone, where the bubbles of hydrocarbon vapor may disengage from the liquid reaction medium. The process may further comprise withdrawing at least a portion of the hydrocarbon vapor from the ionic liquid alkylation zone, condensing the withdrawn hydrocarbon vapor to provide a condensed hydrocarbon liquid stream, and recycling the condensed hydrocarbon liquid stream to the ionic liquid alkylation zone.

In an embodiment, the condensed hydrocarbon liquid stream may be recycled to the ionic liquid alkylation zone by combining the condensed hydrocarbon liquid stream, en masse, with an olefin feed stream and an isobutane recycle stream to provide a combined feed stream. That is to say, in an embodiment the condensed hydrocarbon liquid stream may be combined with the olefin feed stream and the isobutane recycle stream, without any fractionation of the condensed hydrocarbon liquid stream. The process may still further comprise injecting the combined feed stream into the ionic liquid alkylation zone via at least one hydrocarbon feed injection unit.

In an embodiment, the step of injecting the combined feed stream into the ionic liquid alkylation zone may comprise injecting the combined feed stream into the ionic liquid alkylation zone in an upward direction. In an embodiment, the liquid reaction medium may flow upward within the ionic liquid alkylation zone at a location above each hydrocarbon feed injection unit. Such upward flow of the liquid reaction medium may be sufficient to suspend droplets of ionic liquid catalyst in the liquid reaction medium.

In an embodiment, the condensed hydrocarbon liquid stream may comprise a $C_3$-$C_4$ hydrocarbon selected from propane, isobutane, n-butane, and combinations thereof. In an embodiment, the propane and the isobutane may be recycled to the ionic liquid alkylation zone together via (i.e., as components of) the condensed hydrocarbon liquid stream. In an embodiment, the condensed hydrocarbon liquid stream may be merged with the hydrocarbon feed stream, e.g., to provide the combined feed stream, at a location upstream from the ionic liquid alkylation zone.

In an embodiment, the process may further comprise injecting the ionic liquid catalyst into the ionic liquid alkylation zone via a plurality of ionic liquid injection nozzles. Such injection of the ionic liquid catalyst may provide a liquid reaction medium comprising ionic liquid catalyst droplets dispersed in a liquid hydrocarbon continuous phase in the ionic liquid alkylation zone.

According to a further embodiment, a process may comprise injecting a combined feed stream into an ionic liquid alkylation zone, wherein the combined feed stream may comprise at least one $C_4$-$C_{10}$ isoparaffin and at least one $C_2$-$C_{10}$ olefin. The process may further include injecting an ionic liquid catalyst into the ionic liquid alkylation zone via at least one ionic liquid injection nozzle. The process may still further include contacting the at least one isoparaffin and the at least one olefin with the ionic liquid catalyst in the ionic liquid alkylation zone under ionic liquid alkylation conditions to perform an exothermic ionic liquid alkylation reaction. The ionic liquid alkylation reaction may be performed in a liquid reaction medium contained within the ionic liquid alkylation zone. The liquid reaction medium may comprise droplets of ionic liquid catalyst dispersed in a liquid hydrocarbon phase.

The process may yet further include vaporizing a portion of at least one hydrocarbon component of the combined feed stream to provide hydrocarbon vapor in the ionic liquid alkylation zone. In an embodiment, the at least one hydrocarbon may be vaporized via the heat of reaction of the exothermic ionic liquid alkylation reaction. Such hydrocarbon vaporization may comprise forming bubbles of the hydrocarbon vapor within the liquid reaction medium, wherein at least a portion of the bubbles of hydrocarbon vapor may rise through the liquid reaction medium to a top portion of the ionic liquid alkylation zone. In an embodiment, the process may further comprise pneumatically agitating the liquid reaction medium via the bubbles of hydrocarbon vapor. As an example, the formation and movement of the bubbles of hydrocarbon vapor within the liquid reaction medium may cause turbulence sufficient to mix the ionic liquid catalyst and liquid hydrocarbon components of the liquid reaction medium.

The process may further include withdrawing at least a portion of the hydrocarbon vapor from the ionic liquid alkylation zone, wherein the hydrocarbon vapor may comprise a $C_3$-$C_4$ hydrocarbon selected from propane, isobutane, n-butane, and combinations thereof. In an embodiment, the hydrocarbon vapor may be withdrawn from the top portion of the ionic liquid alkylation zone. The process may further include condensing the withdrawn hydrocarbon vapor to provide a condensed hydrocarbon liquid stream. The process may further include merging the condensed hydrocarbon liquid stream with an olefin feed stream and an isobutane recycle stream to provide the combined feed stream. In an embodiment, the combined feed stream may comprise the olefin feed stream, the isobutane recycle stream, the condensed hydrocarbon liquid stream, and an isoparaffin feed stream.

In an embodiment, the process may further include withdrawing aliquots of liquid reaction medium from the ionic liquid alkylation zone to provide a reactor effluent stream. In an embodiment, the liquid reaction medium may comprise, inter alia, an alkylate product, ionic liquid catalyst, and isobutane. In an embodiment, the liquid reaction medium may be withdrawn from a basal portion of the ionic liquid alkylation zone. In another embodiment, liquid reaction medium may be withdrawn from a lateral reactor effluent outlet. In an embodiment, the level of the liquid reaction medium in the ionic liquid alkylation zone may be controlled by "overflow" from the lateral reactor effluent outlet. In another embodiment, the level of the liquid reaction medium may be controlled by a level control valve in communication with a level gauge (see, e.g., FIG. 6).

The process may still further include separating the reactor effluent stream into an ionic liquid phase and a hydrocarbon phase, and fractionating the hydrocarbon phase to provide the isobutane recycle stream and an alkylate product. In an embodiment, the hydrocarbon phase may be fractionated, e.g., to provide the isobutane recycle stream and the alkylate product, via a fractionation unit comprising one or more distillation columns.

Systems and apparatus for ionic liquid catalyzed hydrocarbon conversion, including alkylation for gasoline production, will now be described with reference to the drawings.

FIG. 1 schematically represents a system and process for ionic liquid catalyzed hydrocarbon conversion, such as alkylation. System 100 may comprise an ionic liquid reactor 200 and a hydrocarbon vapor recovery unit 300. During an ionic liquid catalyzed alkylation process a hydrocarbon feed stream 20 may be fed, e.g., injected, into ionic liquid reactor 200, and at the same time an ionic liquid catalyst 42 may be introduced, e.g., injected, into ionic liquid reactor 200, such that the ionic liquid catalyst contacts the hydrocarbon feed stream. Ionic liquid reactor 200 may be configured for performing ionic liquid catalyzed hydrocarbon conversion reactions, such as ionic liquid catalyzed alkylation for alkylate gasoline production. Such reactions may occur within ionic liquid reactor 200 in the liquid phase. Ionic liquid reactor 200 may define, and may be referred to herein as, an ionic liquid alkylation zone.

Hydrocarbon vapor, e.g., comprising $C_3$-$C_4$ hydrocarbons, may be formed in ionic liquid reactor 200 due to heat of reaction generated within ionic liquid reactor 200. Ionic liquid reactor 200 may comprise a hydrocarbon vapor outlet 201. Hydrocarbon vapor outlet 201 may be configured for withdrawing hydrocarbon vapor from ionic liquid reactor 200. Hydrocarbon vapor outlet 201 may be disposed at top of ionic liquid reactor 200 for withdrawing hydrocarbon vapor in the substantial absence of liquid reaction medium.

Hydrocarbon vapor recovery unit 300 may be in fluid communication with ionic liquid reactor 200, via hydrocarbon vapor outlet 201, for receiving withdrawn hydrocarbon vapor 30 from ionic liquid reactor 200. Hydrocarbon vapor recovery unit 300 may be configured for condensing withdrawn hydrocarbon vapor to provide a condensed hydrocarbon liquid stream 20b. System 100 may be configured for recycling the condensed hydrocarbon liquid stream 20b to ionic liquid reactor 200. During an ionic liquid catalyzed alkylation process, a liquid reaction medium 21 may be withdrawn from ionic liquid reactor 200, and a product, e.g., alkylate, may be separated from the withdrawn liquid reaction medium 21.

Figure 2:
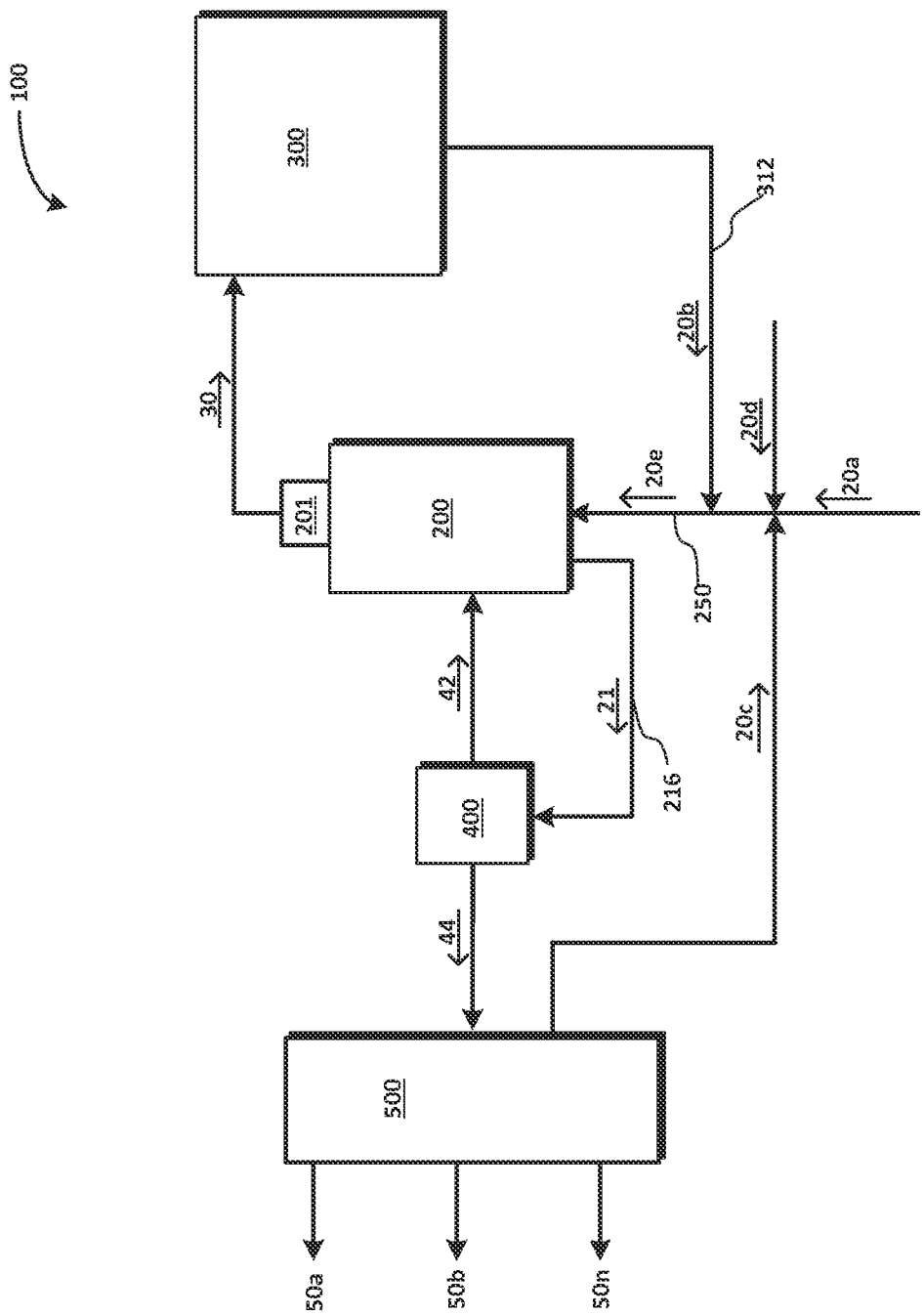
FIG. 2 schematically represents a system and process for ionic liquid catalyzed hydrocarbon conversion including a fractionation unit, according to an embodiment of the present invention.

FIG. 2 schematically represents a system and process for ionic liquid catalyzed hydrocarbon conversion including a fractionation unit, according to another embodiment. System 100 as shown in FIG. 2 may comprise an ionic liquid reactor 200, a hydrocarbon vapor recovery unit 300 in fluid communication with ionic liquid reactor 200, a hydrocarbon/ionic liquid in fluid communication with ionic liquid reactor 200, and a fractionation unit 500 in fluid communication with hydrocarbon/ionic liquid separator 400. Hydrocarbon vapor 30 may be withdrawn from ionic liquid reactor 200 via hydrocarbon vapor outlet 201 and fed to hydrocarbon vapor recovery unit 300 to provide a condensed hydrocarbon liquid stream 20b. Condensed hydrocarbon liquid stream 20b may be recycled to ionic liquid reactor 200 via a condensed hydrocarbon liquid conduit 312. In an embodiment, a combined feed stream 20e to ionic liquid reactor 200 may comprise an olefin feed stream 20a, condensed hydrocarbon liquid stream 20b, and an isobutane recycle stream 20c. In an embodiment, combined feed stream 20e may further comprise an isoparaffin feed stream 20d. Combined feed stream 20e may be fed to ionic liquid reactor 200 via a hydrocarbon feed injection conduit 250.

With further reference to FIG. 2, liquid reaction medium 21 may be withdrawn from ionic liquid reactor 200 to provide an effluent stream to hydrocarbon/ionic liquid separator 400 via a line 216. The ionic liquid phase may be returned to ionic liquid reactor 200, regenerated, or reserved for future use, as appropriate. The hydrocarbon phase 44 may be fractionated via fractionation unit 500 to provide isobutane recycle stream 20c, as well as fractions 50a-50n that may include, for example, an alkylate product.

Figure 3:
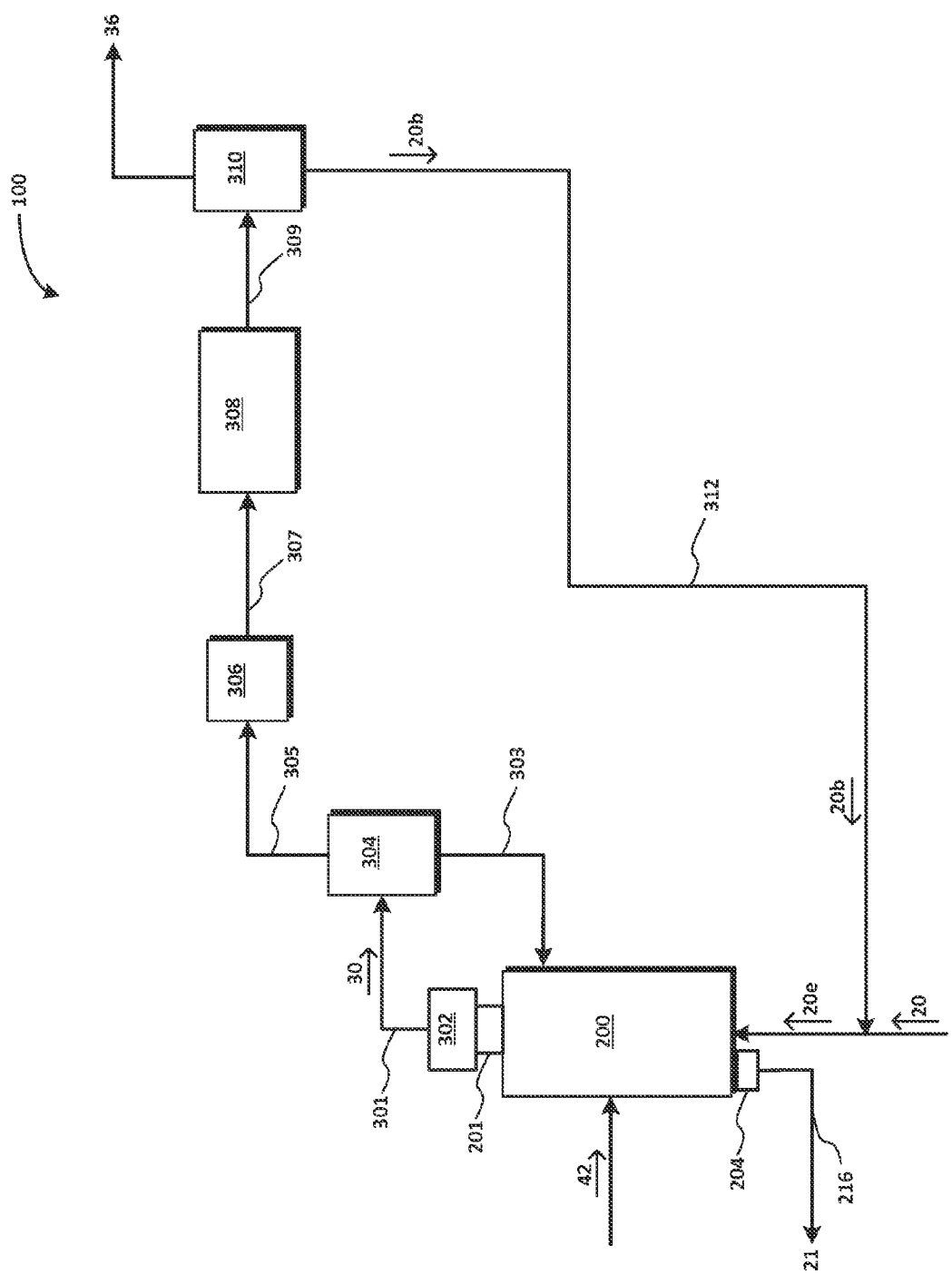
FIG. 3 schematically represents a system and process for ionic liquid catalyzed hydrocarbon conversion showing components of a hydrocarbon vapor recovery unit, according to an embodiment of the present invention.

FIG. 3 schematically represents a system 100 and a process for ionic liquid catalyzed hydrocarbon conversion, showing components of a hydrocarbon vapor recovery unit, according to another embodiment. In an embodiment, such process may comprise ionic liquid catalyzed alkylation. During ionic liquid catalyzed alkylation, a hydrocarbon feed stream may be fed to ionic liquid reactor 200. In an embodiment, the hydrocarbon feed stream may comprise a combined feed stream 20e, e.g., as described hereinabove with reference to FIG. 2. At the same time, ionic liquid catalyst 42 may be injected into ionic liquid reactor 200. Ionic liquid reactor 200 may comprise a hydrocarbon vapor outlet 201.

The hydrocarbon conversion reaction in ionic liquid reactor 200, e.g., alkylation, may be exothermic. Conditions (e.g., temperature, pressure) within ionic liquid reactor may be selected such that the hydrocarbon components of the liquid reaction medium remain in the liquid phase in the absence of heat of reaction generated by the alkylation reaction. Hydrocarbon vapor may then be produced, e.g., at certain loci, within ionic liquid reactor 200 as a result of heat generated during the reaction. A portion of the thus generated hydrocarbon vapor may be withdrawn from ionic liquid reactor 200 via hydrocarbon vapor outlet 201. The hydrocarbon vapor may contain entrained ionic liquid droplets. The hydrocarbon vapor may be passed through a demister unit 302. Demister unit 302 may be configured for removing entrained droplets of ionic liquid catalyst from the hydrocarbon vapor stream 30. In an embodiment, demister unit 302 may comprise demist packing material (not shown). Coalesced droplets of ionic liquid may be returned to ionic liquid reactor 200, e.g., via gravity.

In the embodiment of FIG. 3, system 100 may include ionic liquid reactor 200 and a hydrocarbon vapor recovery unit in fluid communication with ionic liquid reactor 200, wherein the hydrocarbon vapor recovery unit may comprise a vapor/entrained liquid separator 304, a gas compressor 306, a heat exchanger 308, and a gas/condensed liquid separator 310. The withdrawn hydrocarbon vapor 30 may be passed via a line 301 to vapor/entrained liquid separator 304 where any residual entrained liquid droplets may be removed from the hydrocarbon vapor. Vapor/entrained liquid separator 304 may also be referred to herein as a first gas/liquid separator. Ionic liquid catalyst and/or other liquid(s) captured by vapor/entrained liquid separator 304 may be returned to ionic liquid reactor 200 via a line 303.

The withdrawn hydrocarbon vapor may be passed from vapor/entrained liquid separator 304 via a line 305 to gas compressor 306 to compress the withdrawn hydrocarbon vapor. The compressed hydrocarbon vapor may be passed from gas compressor 306 via a line 307 to heat exchanger 308 for cooling the compressed hydrocarbon vapor. In an embodiment, heat exchanger 308 may comprise a shell and tube heat exchanger. A condensed hydrocarbon liquid stream may be passed from heat exchanger 308 via a line 309 to a gas/condensed liquid separator 310 to remove non-condensable gases 36 from the condensed hydrocarbon liquid stream 20b. Gas/condensed liquid separator 310 may also be referred to herein as a second gas/liquid separator. It is to be understood that hydrocarbon vapor recovery from, and recycling to, ionic liquid reactor 200 is not limited to the configuration shown in FIG. 3.

In an embodiment, non-condensable gases 36, which may comprise $H_2$ and HCl, may be passed to an isostripper (not shown). The condensed hydrocarbon liquid stream 20b may be recycled to ionic liquid reactor 200, e.g., via a condensed hydrocarbon liquid conduit 312. In an embodiment, condensed hydrocarbon liquid stream 20b may be combined with a hydrocarbon feed stream 20, e.g., comprising an olefin feed stream, to provide combined feed stream 20e (e.g., as shown in FIG. 2). In an embodiment, condensed hydrocarbon liquid stream 20b may be recycled to ionic liquid reactor 200 by injecting combined feed stream 20e into ionic liquid reactor 200. A portion of liquid reaction medium 21 may be withdrawn from ionic liquid reactor 200, e.g., via a basal reactor effluent outlet 204 and a reactor effluent line 216.

Figure 4:
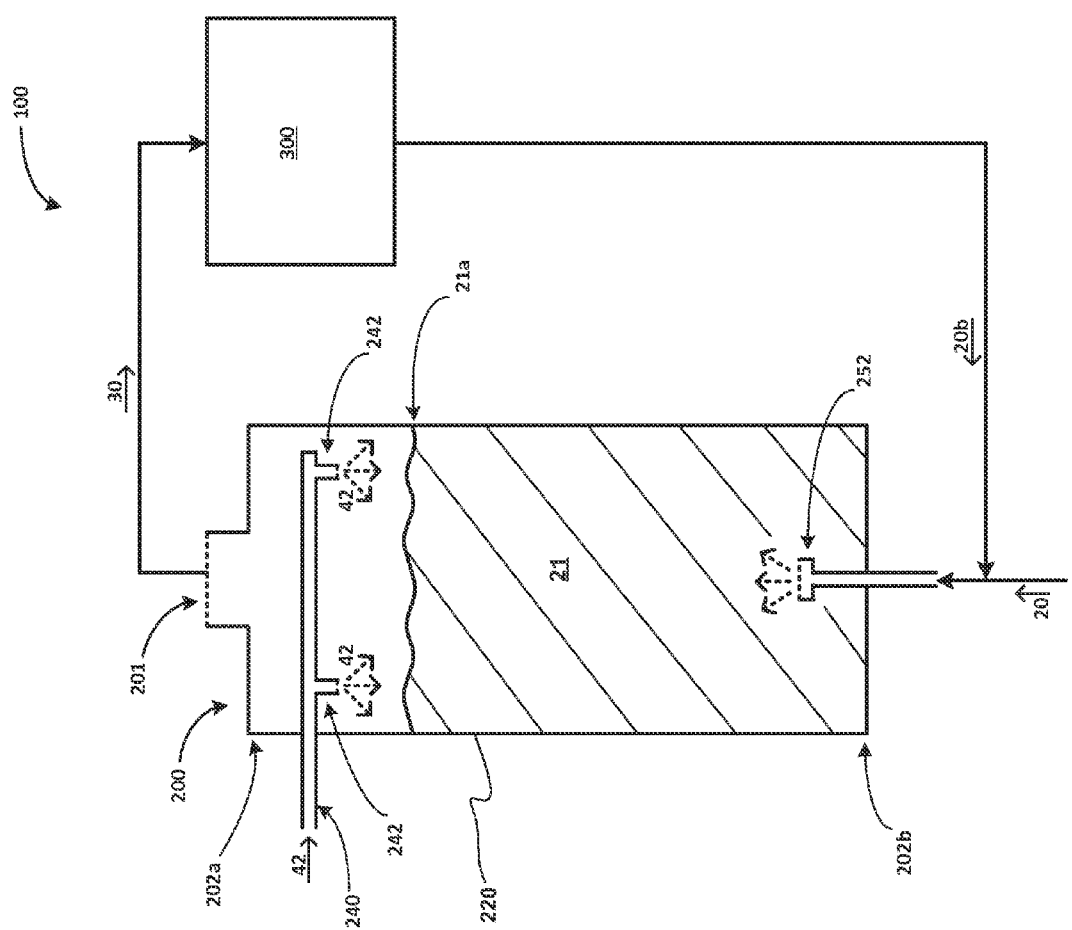
FIG. 4 schematically represents a system and process for ionic liquid catalyzed hydrocarbon conversion including hydrocarbon recycling from a hydrocarbon vapor recovery unit, according to an embodiment of the present invention.

FIG. 4 schematically represents a system 100 and a process for ionic liquid catalyzed hydrocarbon conversion, according to another embodiment. System 100 may include ionic liquid reactor 200 and a hydrocarbon vapor recovery unit 300 in fluid communication with ionic liquid reactor 200. Ionic liquid reactor 200 may comprise a reactor wall 220 and a hydrocarbon vapor outlet 201. In an embodiment, ionic liquid reactor 200 may be substantially cylindrical. Ionic liquid reactor 200 may be vertically oriented, and may include a reactor top 202a and a reactor base 202b. Hydrocarbon vapor outlet 201 may be disposed at reactor top 202a. Ionic liquid catalyst 42 may be introduced into ionic liquid reactor 200 via an ionic liquid injection conduit 240 and ionic liquid injection nozzles 242.

Ionic liquid reactor 200 may contain a liquid reaction medium 21. Liquid reaction medium 21 may comprise droplets of ionic liquid catalyst dispersed in a liquid hydrocarbon continuous phase. During an ionic liquid alkylation process, heat of reaction may be generated sufficient to vaporize at least one hydrocarbon component within liquid reaction medium 21. The resulting hydrocarbon vapor may be withdrawn from ionic liquid reactor 200 via hydrocarbon vapor outlet 201, and a stream of hydrocarbon vapor 30 may be passed to hydrocarbon vapor recovery unit 300 to provide a condensed hydrocarbon liquid stream 20b.

With further reference to FIG. 4, condensed hydrocarbon liquid stream 20b may be recycled to ionic liquid reactor from hydrocarbon vapor recovery unit 300. Ionic liquid reactor 200 may include at least one hydrocarbon feed injection unit 252. In an embodiment, condensed hydrocarbon liquid stream 20b may be combined with hydrocarbon feed stream 20 and the combined stream may be injected into ionic liquid reactor 200 via hydrocarbon feed injection unit 252. Other numbers and configurations for hydrocarbon feed injection unit(s) 252 are also contemplated (see, e.g., FIGS. 13A-13C and 14A-15B).

Although ionic liquid injection nozzles 242 are shown in FIG. 4 as being above the level 21a of liquid reaction medium 21, the injection of ionic liquid catalyst at-, above-, or below the level of liquid reaction medium 21 is also possible. Other numbers and configurations for ionic liquid injection nozzles 242 are also contemplated (see, e.g., FIGS. 13A-13C and 14A-15B).

Figure 5:
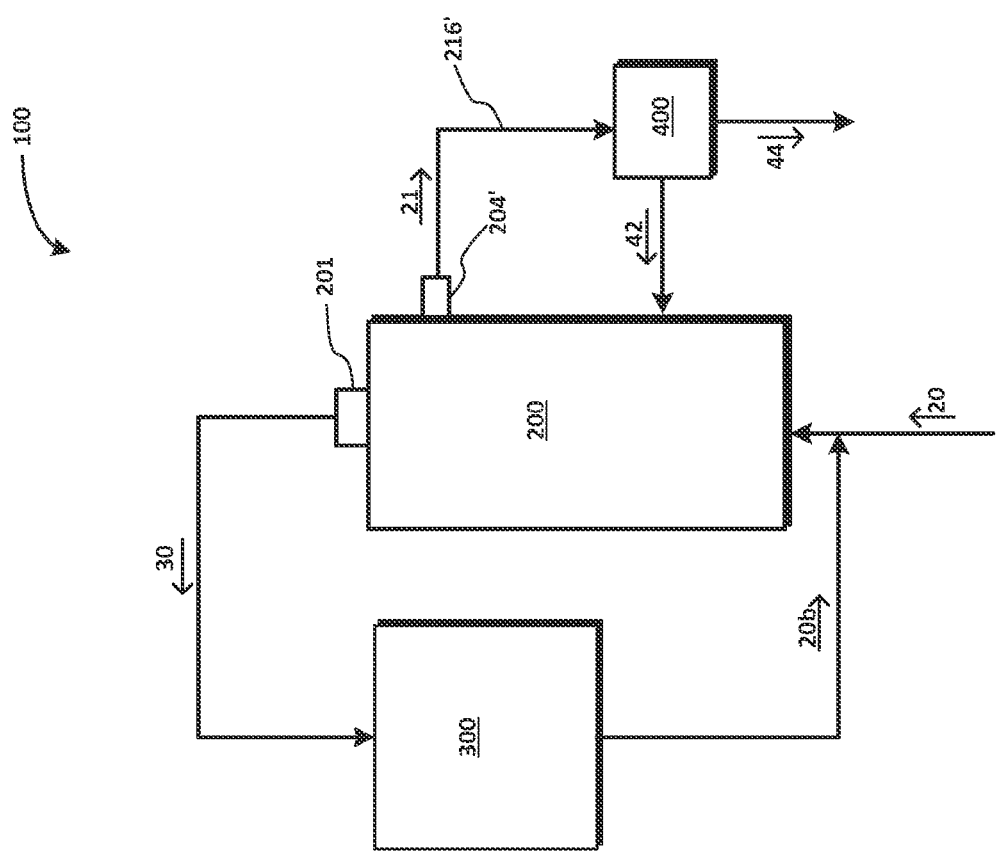
FIG. 5 schematically represents a system and process for ionic liquid catalyzed hydrocarbon conversion showing lateral withdrawal of liquid reaction medium, according to an embodiment of the present invention.

FIG. 5 schematically represents a system 100 and a process for ionic liquid catalyzed hydrocarbon conversion. System 100 may comprise an ionic liquid reactor 200, a hydrocarbon/ionic liquid separator 400, and a hydrocarbon vapor recovery unit 300 in fluid communication with ionic liquid reactor 200. Ionic liquid reactor 200 may comprise hydrocarbon vapor outlet 201. In an embodiment, ionic liquid reactor 200 may be substantially cylindrical and ionic liquid reactor 200 may be vertically oriented.

With further reference to FIG. 5, ionic liquid reactor 200 may further comprise a lateral reactor effluent outlet 204'. Aliquots of liquid reaction medium 21 may be withdrawn from ionic liquid reactor 200 via 204' and passed via a reactor effluent line 216' to hydrocarbon/ionic liquid separator 400 to provide an ionic liquid phase comprising ionic liquid catalyst 42 and a hydrocarbon phase 44 comprising isobutane and an alkylate product. Ionic liquid catalyst 42 may be recycled to ionic liquid reactor 200. Hydrocarbon phase 44 may be passed to a fractionation unit 500 (see, e.g., FIG. 2). In an embodiment, the level 21a of the liquid reaction medium 21 (see, e.g., FIG. 4) in ionic liquid reactor 200 may be controlled by "overflow" from lateral reactor effluent outlet 204'. A condensed hydrocarbon liquid stream 20b from hydrocarbon vapor recovery unit 300 may be recycled to ionic liquid reactor 200. In an embodiment, condensed hydrocarbon liquid stream 20b may be combined with a hydrocarbon feed stream 20 and the combined feed stream may be injected into ionic liquid reactor 200.

Figure 6:
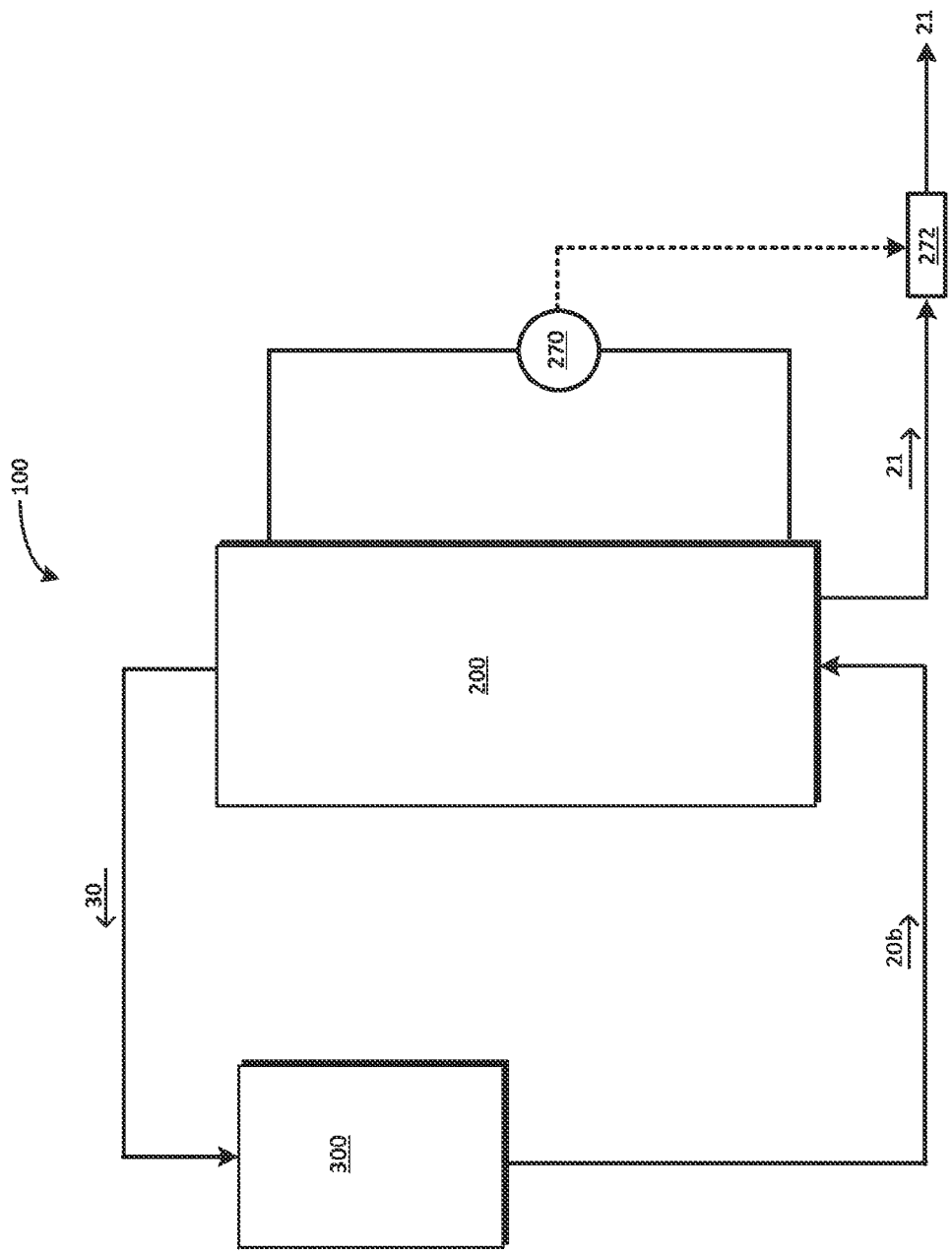
FIG. 6 schematically represents a system and process for ionic liquid catalyzed hydrocarbon conversion including a level gauge and control valve, according to an embodiment of the present invention.

FIG. 6 schematically represents a system 100 and a process for ionic liquid catalyzed hydrocarbon conversion, according to another embodiment. System 100 may comprise an ionic liquid reactor 200 and a hydrocarbon vapor recovery unit 300 in fluid communication with ionic liquid reactor 200. Hydrocarbon vapor 30 may be passed from ionic liquid reactor 200 to hydrocarbon vapor recovery unit 300 to provide a condensed hydrocarbon liquid stream 20b for recycling to ionic liquid reactor 200, essentially as described herein for other embodiments. Ionic liquid reactor 200 may contain liquid reaction medium 21 (see, e.g., FIG. 4).

System 100 of FIG. 6 may further comprise a level gauge 270 and an effluent control valve 272 in signal communication with level gauge 270. Level gauge 270 is in communication with ionic liquid reactor 200 for monitoring the level 21a (see, e.g., FIG. 4) of liquid reaction medium 21 in ionic liquid reactor 200. Level gauge 270 may signal effluent control valve 272 so as to control the level 21a of liquid reaction medium 21 in ionic liquid reactor 200. Liquid reaction medium 21 withdrawn from ionic liquid reactor may be phase separated prior to fractionation of the hydrocarbon phase to provide one or more products, e.g., as described with reference to FIG. 2.

Figure 7:
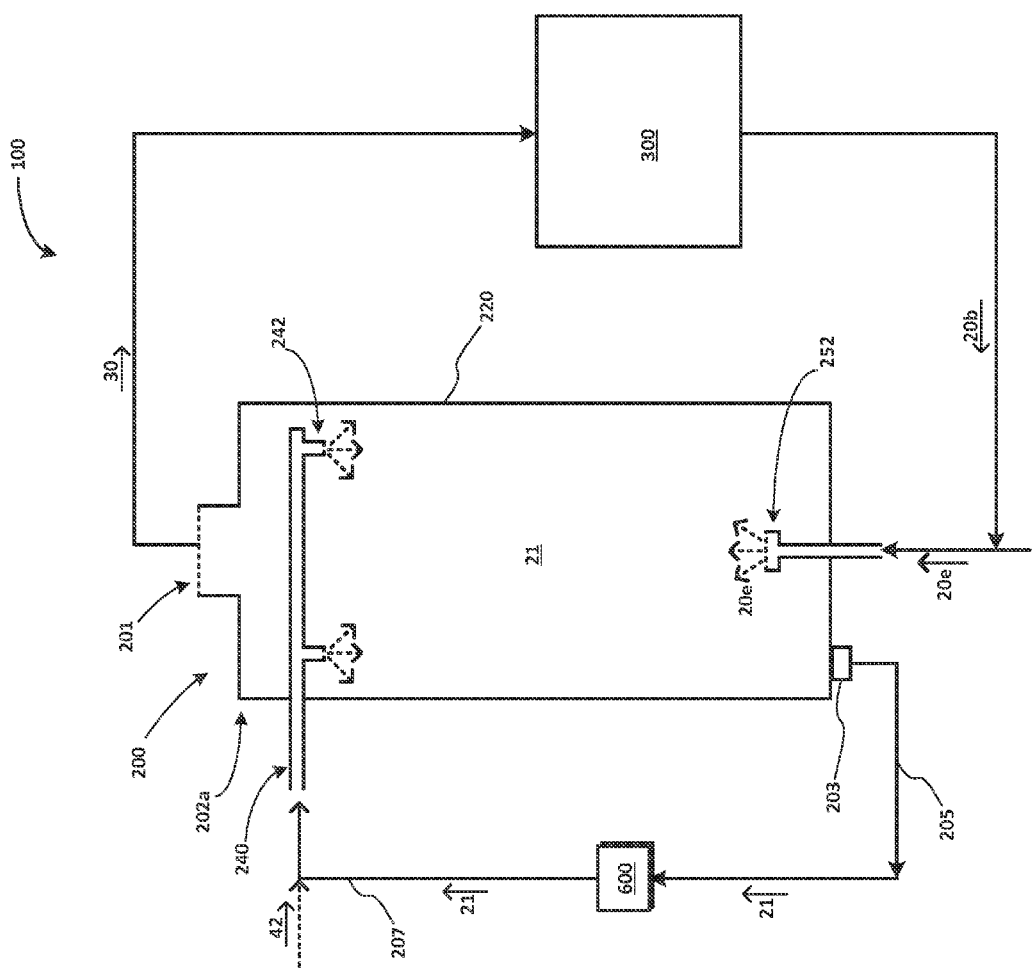
FIG. 7 schematically represents a system and process for ionic liquid catalyzed hydrocarbon conversion showing liquid reaction medium recycling, according to an embodiment of the present invention.

FIG. 7 schematically represents a system 100 and a process for ionic liquid catalyzed hydrocarbon conversion, according to another embodiment. System 100 may comprise an ionic liquid reactor 200 and a hydrocarbon vapor recovery unit 300 in fluid communication with ionic liquid reactor 200. Hydrocarbon vapor 30 may be passed from ionic liquid reactor 200 via hydrocarbon vapor outlet 201 to hydrocarbon vapor recovery unit 300 to provide a condensed hydrocarbon liquid stream 20b for recycling to ionic liquid reactor 200, essentially as described herein with respect to other embodiments. Condensed hydrocarbon liquid stream 20b may be recycled to ionic liquid reactor 200 as part of a combined feed stream 20e for injection into ionic liquid reactor 200 via at least one hydrocarbon feed injection unit 252.

Ionic liquid reactor 200 may contain liquid reaction medium 21. In the embodiment of FIG. 7, ionic liquid reactor 200 may further comprise a liquid recycle outlet 203 configured for withdrawing liquid reaction medium 21 from ionic liquid reactor 200. Ionic liquid reactor 200 may be vertically oriented. In an embodiment, liquid recycle outlet 203 may be disposed at a lower or basal portion of the ionic liquid reactor, and in a sub-embodiment, liquid recycle outlet 203 may be located at the base of ionic liquid reactor 200. Liquid reaction medium 21 may be recycled to ionic liquid reactor 200 via a liquid recycle pump 600 and a line 207. Line 207 may be in fluid communication with ionic liquid injection conduit 240 and ionic liquid injection nozzles 242. The recycled liquid reaction medium 21 may be injected into ionic liquid reactor 200 via ionic liquid injection nozzles 242. In an embodiment, the recycled liquid reaction medium 21 may be injected into ionic liquid reactor 200 together with ionic liquid catalyst 42, which may be phase separated ionic liquid catalyst, regenerated ionic liquid catalyst, or fresh ionic liquid catalyst.

Figure 8:
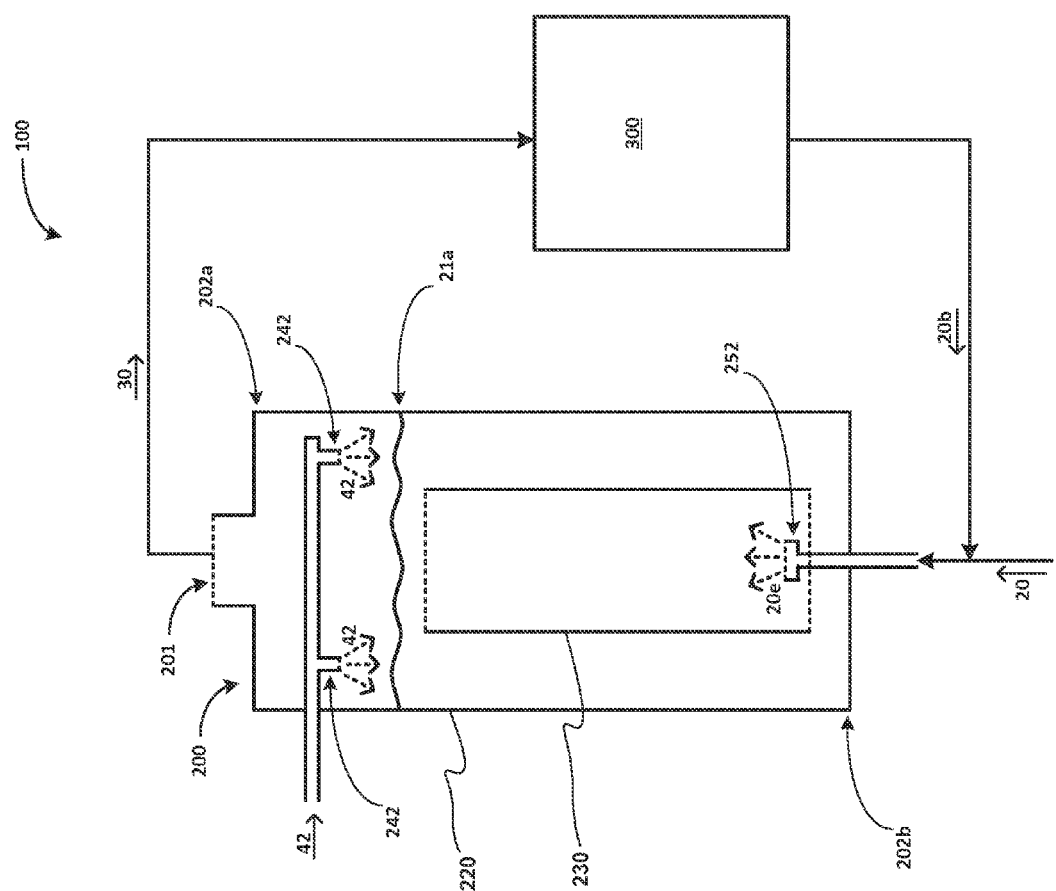
FIG. 8 schematically represents a system and process for ionic liquid catalyzed hydrocarbon conversion including a draft tube within an ionic liquid reactor, according to an embodiment of the present invention.

FIG. 8 schematically represents a system 100 and a process for ionic liquid catalyzed hydrocarbon conversion, according to another embodiment. System 100 may comprise components and features in common with other embodiments described herein, including an ionic liquid reactor 200 and a hydrocarbon vapor recovery unit 300 in fluid communication with ionic liquid reactor 200 for condensing hydrocarbon vapor 30 and for recycling condensed hydrocarbon liquid stream 20*b* to ionic liquid reactor 200.

In the embodiment of FIG. 8, ionic liquid reactor 200 may be vertically oriented. Ionic liquid reactor 200 may comprise a substantially cylindrical reactor wall 220. In the embodiment of FIG. 8, system 100 may further comprise a draft tube 230 disposed within ionic liquid reactor 200. Draft tube 230 and reactor wall 220 may jointly define an inner zone and an outer zone of ionic liquid reactor 200 (see, e.g., FIGS. 9A-9D). In an embodiment, draft tube 230 may be disposed coaxially with reactor wall 220. In an embodiment, reactor wall 220 may extend above and/or below draft tube 230. Typically, draft tube 230 will be submerged by liquid reaction medium 21, i.e., disposed below level 21*a* of liquid reaction medium 21, during ionic liquid catalyzed alkylation processes. Draft tube 230 may promote the circulation and mixing of liquid reaction medium 21 within ionic liquid reactor 200.

In an embodiment, at least one hydrocarbon feed injection unit 252 may be disposed within draft tube 230. In an embodiment, at least one hydrocarbon feed injection unit 252 may be coaxial with draft tube 230 and ionic liquid reactor 200. In an embodiment, ionic liquid reactor 200 may further comprise a plurality of ionic liquid injection nozzles 242 for injecting ionic liquid catalyst 42 into ionic liquid reactor 200. In the embodiment of FIG. 8, each of ionic liquid injection nozzles 242 may be disposed external to draft tube 230. In an embodiment, each of ionic liquid injection nozzles 242 may be disposed above draft tube 230. In an embodiment, the ratio of the draft tube diameter to the reactor wall diameter may be in the range from 0.1-0.9, or from 0.5-0.8.

FIG. 9A schematically represents an ionic liquid reactor 200 including a draft tube 230, and FIG. 9B shows the ionic liquid reactor of FIG. 9A as seen along the line 9B-9B, according to another embodiment. Ionic liquid reactor 200 may be vertically oriented. Ionic liquid reactor 200 may comprise a reactor top 202*a*, a reactor base 202*b*, and a reactor wall 220. Reactor wall 220 may be substantially cylindrical. In the embodiment of FIGS. 9A-9B, ionic liquid reactor 200 may further comprise a draft tube 230 disposed within ionic liquid reactor 200. Draft tube 230 may be at least substantially cylindrical. Draft tube 230 may define an inner zone, IZ, within draft tube 230; draft tube 230 and reactor wall 220 may jointly define an outer zone, OZ, external to draft tube 230. In an embodiment, draft tube 230 may be disposed coaxially with ionic liquid reactor 200/reactor wall 220.

FIG. 9C schematically represents a vertically oriented ionic liquid reactor 200, and FIG. 9D shows ionic liquid reactor 200 of FIG. 9C as seen along the line 9D-9D, according to another embodiment. Ionic liquid reactor 200 may be substantially cylindrical. Ionic liquid reactor 200 may include an inner zone, IZ, and an outer zone, OZ. Inner zone, IZ, and outer zone, OZ, may correspond to inner and outer portions, respectively of ionic liquid reactor 200. In an embodiment, inner zone, IZ, may be substantially cylindrical and outer zone, OZ, may be substantially annular. In embodiments of an ionic liquid reactor 200 having a draft tube 230, inner zone, IZ, may correspond to a region of ionic liquid reactor 200 within the draft tube 230, and the outer zone, OZ, may correspond to a region of ionic liquid reactor 200 external to the draft tube 230 (i.e., disposed between draft tube 230 and reactor wall 220). However, embodiments of an ionic liquid reactor 200 lacking a draft tube can similarly have both inner zone, IZ, and outer zone, OZ, therewithin.

As noted hereinabove, a draft tube disposed within ionic liquid reactor 200 will typically be shorter than ionic liquid reactor 200 such that reactor wall 220 may extend above the top of the draft tube and/or below the bottom of the draft tube. However, for the purpose of describing the location of inner zone, IZ, and outer zone, OZ, herein, e.g., with respect to the configuration of hydrocarbon feed units 252 and ionic liquid injection nozzles 242, inner zone, IZ, and outer zone, OZ, may both be considered to extend above and/or below the ends of the draft tube (if any), such as over the entire length (height) of ionic liquid reactor 200 (see, e.g., FIG. 9C).

FIG. 10A schematically represents an ionic liquid reactor 200 including a draft tube 230, and FIG. 10B shows the ionic liquid reactor of FIG. 10A as seen along the line 10B-10B, according to another embodiment. With reference to FIGS. 10A-10B, ionic liquid reactor 200 may be vertically oriented. Ionic liquid reactor 200 may comprise a reactor top 202*a*, a reactor base 202*b*, and a reactor wall 220. Ionic liquid reactor 200 and reactor wall 220 may be substantially cylindrical. In the embodiment of FIGS. 10A-10B, ionic liquid reactor 200 may further comprise a draft tube 230 disposed within ionic liquid reactor 200. Draft tube 230 may be vertically oriented and may be disposed coaxially with reactor wall 220. In an embodiment, draft tube 230 may include tapered walls. In an embodiment, draft tube 230 may include an enlarged draft tube upper portion 230*a*, and a substantially cylindrical draft tube lower portion 230*b*. In a sub-embodiment, enlarged upper portion 230*a* of draft tube 230 may be substantially frusto-conical in configuration.

Figure 11:
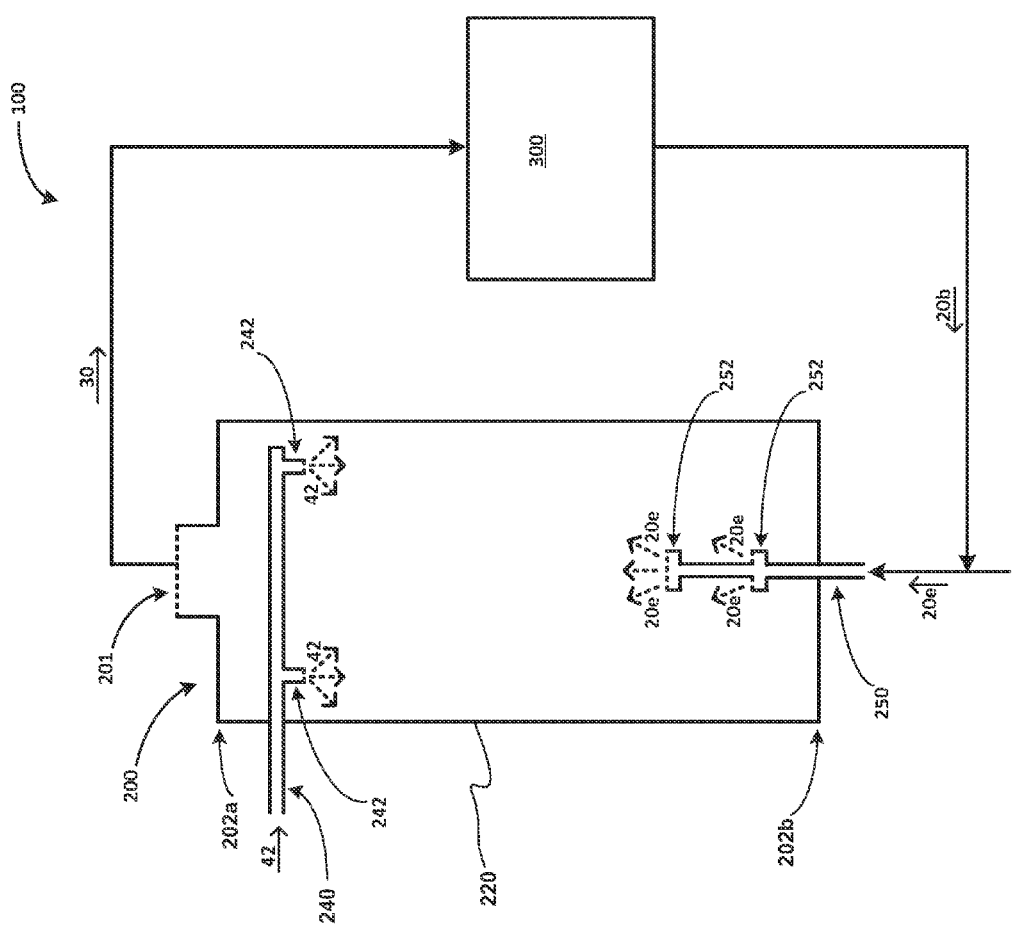
FIG. 11 schematically represents a process and a system including an ionic liquid reactor having vertically spaced hydrocarbon feed injection units, according to an embodiment of the present invention.

FIG. 11 schematically represents a system 100 and a process for ionic liquid catalyzed hydrocarbon conversion, according to another embodiment. System 100 may comprise an ionic liquid reactor 200 and a hydrocarbon vapor recovery unit 300 in fluid communication with ionic liquid reactor 200. In an embodiment, ionic liquid reactor 200 may be vertically oriented. Ionic liquid reactor 200 may comprise a reactor top 202*a*, a reactor base 202*b*, a reactor wall 220, and a hydrocarbon vapor outlet 201. Hydrocarbon vapor 30 may be passed from ionic liquid reactor 200 via hydrocarbon vapor outlet 201 to hydrocarbon vapor recovery unit 300 to provide a condensed hydrocarbon liquid stream 20*b* for recycling to ionic liquid reactor 200, essentially as described herein for other embodiments.

In the embodiment of FIG. 11, a hydrocarbon feed stream 20 may be injected into ionic liquid reactor 200 via a hydrocarbon feed conduit 250 and a plurality of hydrocarbon feed injection units 252, wherein at least two of the hydrocarbon feed injection units 252 may be vertically spaced apart. In an embodiment, the hydrocarbon feed stream may comprise a combined feed stream 20*e*, e.g., as described with reference to FIG. 2. In an embodiment, hydrocarbon feed injection units 252 may be disposed at a basal portion of ionic liquid reactor 200, and hydrocarbon feed injection units 252 may be configured for injecting combined feed stream 20e in an upward direction. In a sub-embodiment, combined feed stream 20e may be introduced into ionic liquid reactor 200 at reactor base 202b.

With further reference to FIG. 11, ionic liquid catalyst 42 may be injected into ionic liquid reactor 200 via a plurality of ionic liquid injection nozzles 242, wherein at least two of ionic liquid injection nozzles 242 may be horizontally spaced apart. As shown in FIG. 11, ionic liquid injection nozzles 242 may be disposed at an upper or top portion of ionic liquid reactor 200, e.g., near reactor top 202a, and ionic liquid injection nozzles 242 may be configured for injecting ionic liquid catalyst 42 in a downward direction. Although two hydrocarbon feed injection units 252 and two ionic liquid injection nozzles 242 are shown in FIG. 11, other numbers and arrangements of both hydrocarbon feed injection units 252 and ionic liquid injection nozzles 242 are possible. Although the embodiment of FIG. 11 indicates the absence of a draft tube within ionic liquid reactor 200, the configuration of hydrocarbon feed injection units 252 and ionic liquid injection nozzles 242 of FIG. 11 may also be used in combination with a draft tube (see, e.g., FIG. 8).

FIGS. 12A-12B schematically represent an ionic liquid reactor, according to another embodiment. Ionic liquid reactor 200 may comprise a hydrocarbon feed injection unit 252 disposed in an inner zone, IZ, of ionic liquid reactor 200. In a sub-embodiment, hydrocarbon feed injection unit 252 may be co-axial with ionic liquid reactor 200. FIG. 12B shows the ionic liquid reactor of FIG. 12A as seen along the line 12B-12B. Reaction conditions in ionic liquid reactor 200 may be maintained such that an ionic liquid alkylation reaction occurs in the liquid phase and hydrocarbon vaporization only occurs at a substantial rate when the reaction rate attains a relatively high rate, e.g., within zones having relatively high concentrations of reactants (hydrocarbon feed).

FIGS. 12A and 12B show a hydrocarbon vaporization zone, VZ, at a location above hydrocarbon feed injection unit 252 within inner zone, IZ, wherein hydrocarbon vaporization zone, VZ, indicates a zone of enhanced hydrocarbon vaporization, as compared with ionic liquid reactor 200 as a whole. In an embodiment, such enhanced hydrocarbon vaporization may be due to the proximity of hydrocarbon feed injection unit 252, and a concomitant higher rate of the exothermic ionic liquid catalyzed alkylation reaction. Higher rates of hydrocarbon vaporization cause turbulence within ionic liquid reactor 200 and promote mixing of the liquid reaction medium 21 (see, e.g., FIGS. 13A-13C). In an embodiment, hydrocarbon vaporization zone, VZ, may indicate a region of maximum liquid velocity within ionic liquid reactor 200. In an embodiment, the mixing and flow of liquid reaction medium 21 within ionic liquid reactor 200 may be greatest within and adjacent to hydrocarbon vaporization zone(s), VZ.

FIG. 12C schematically represents an ionic liquid reactor 200 having a plurality of hydrocarbon feed injection units 252, according to another embodiment. A hydrocarbon vaporization zone, VZ, may be disposed above each hydrocarbon feed injection unit 252, substantially as described with reference to FIGS. 12A-12B, supra. In the embodiment of FIG. 12C, however, each hydrocarbon feed injection unit 252 may be disposed in an outer zone, OZ, of ionic liquid reactor 200. In an embodiment, the direction of flow of liquid reaction medium 21 within ionic liquid reactor 200 may be generally upward at locations above each hydrocarbon feed injection unit 252, regardless of whether hydrocarbon feed injection unit(s) 252 are located in the inner zone, IZ, or the outer zone, OZ, and regardless of whether the ionic liquid reactor contains a draft tube (see, e.g., FIGS. 13A-13C).

It is to be understood that hydrocarbon vaporization zones, VZ, may have configurations other than as specifically shown in FIGS. 12A-12C, e.g., depending on various factors such as the number and configuration of feed injection units 252, the rate of hydrocarbon vaporization within the hydrocarbon vaporization zone and the reaction conditions within ionic liquid reactor 200, as well as pressure differences between ionic liquid reactor 200 and the hydrocarbon feed stream, and the fluid dynamics within ionic liquid reactor 200. It is to be understood further that hydrocarbon vaporization may also occur at various locations within ionic liquid reactor 200 other than in hydrocarbon vaporization zone(s), VZ, albeit typically at lower rates.

FIG. 13A schematically represents a basal portion of a vertically oriented ionic liquid reactor 200, according to another embodiment. Ionic liquid reactor 200 may comprise a reactor top 202a, a reactor base, 202b, a reactor wall 220, a hydrocarbon vapor outlet 201, a plurality of hydrocarbon feed injection units 252, and a plurality of ionic liquid injection nozzles 242. Ionic liquid reactor 200 may further comprise a draft tube 230. Draft tube 230 may be disposed coaxially within ionic liquid reactor 200. The upper or top portion of ionic liquid reactor 200 is omitted from FIGS. 13A-13C for the sake of clarity of illustration.

In the embodiment of FIG. 13A, both the hydrocarbon feed injection units 252 and the ionic liquid injection nozzles 242 may be disposed within inner zone, IZ, of ionic liquid reactor 200. Hydrocarbon feed injection units 252 may be vertically spaced apart, while ionic liquid injection nozzles 242 may be horizontally spaced apart. Ionic liquid catalyst 42 may be introduced into ionic liquid reactor 200 via an ionic liquid injection conduit 240 in fluid communication with each of ionic liquid injection nozzles 242. A hydrocarbon feed stream 20 may be introduced into ionic liquid reactor 200 via a hydrocarbon feed injection conduit 250 in fluid communication with each of hydrocarbon feed injection units 252.

Although the embodiment of FIG. 13A includes draft tube 230 within ionic liquid reactor 200, the configuration of hydrocarbon feed injection units 252 and ionic liquid injection nozzles 242 of FIG. 13A may also be used in the absence of a draft tube. Furthermore, it is to be understood that the concept of an inner zone, IZ, and an outer zone, OZ, of ionic liquid reactor 200 may apply in the absence of a draft tube, as well as in the presence of a draft tube. In the embodiment of FIG. 13A, the general direction of flow of liquid reaction medium 21 within ionic liquid reactor 200 is indicated (arrows) as upward in inner zone, IZ, and downward in outer zone, OZ.

In an embodiment, the circulation of liquid reaction medium 21 within ionic liquid reactor 200 may be driven primarily by enhanced vaporization in regions of ionic liquid reactor 200 located above hydrocarbon feed injection unit(s) 252. Such regions of enhanced hydrocarbon vaporization may be referred to herein as hydrocarbon vaporization zones (see, e.g. FIGS. 12A-12C). In an embodiment, the circulation of liquid reaction medium 21 within ionic liquid reactor 200 may be at least generally similar both in the presence and absence of a draft tube.

Figure 13B:
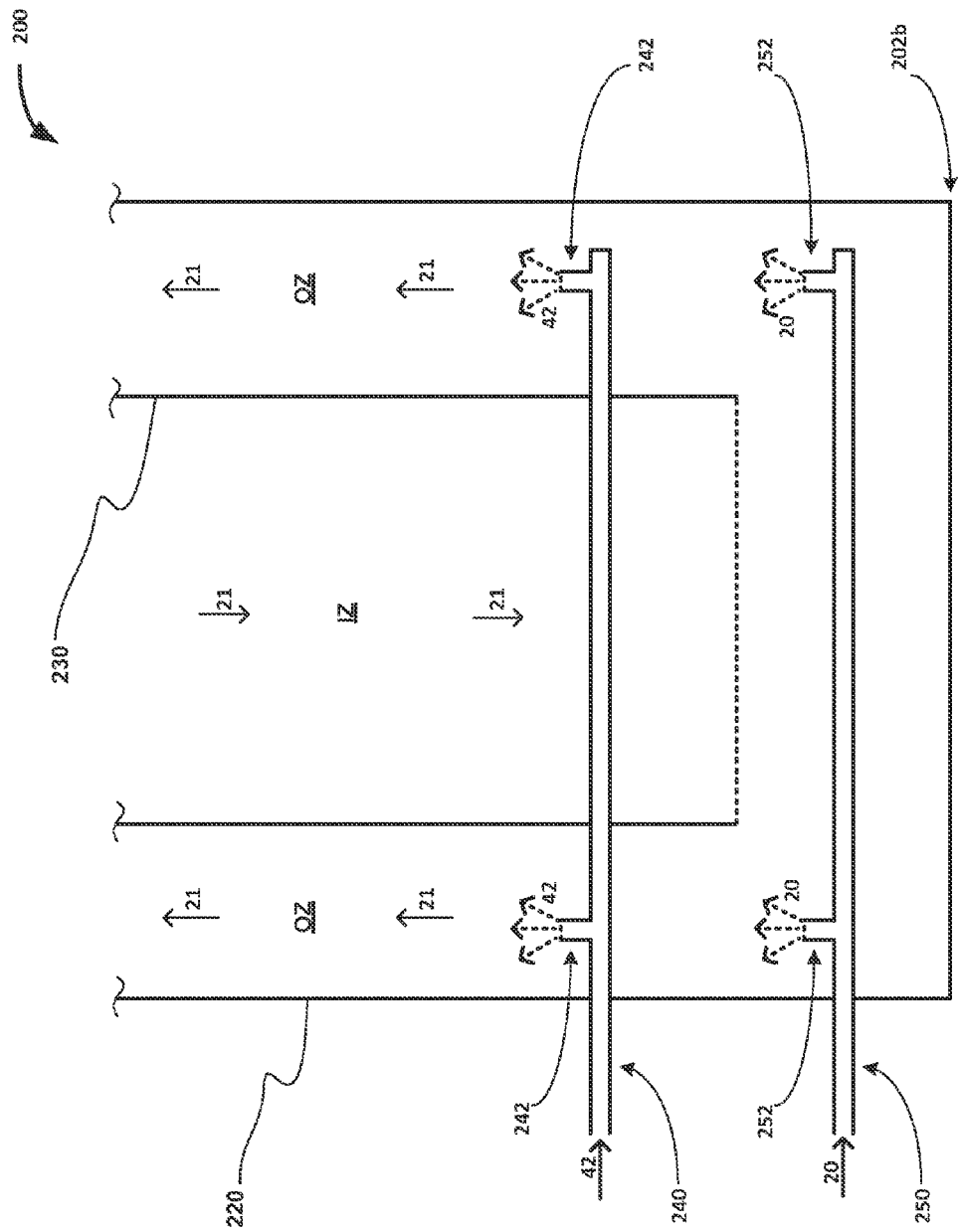
FIG. 13B schematically represents a basal portion of a vertically oriented ionic liquid reactor having horizontally spaced hydrocarbon feed injection units and horizontally spaced ionic liquid injection nozzles in an outer zone of the ionic liquid reactor, according to an embodiment of the present invention.

FIG. 13B schematically represents a basal portion of a vertically oriented ionic liquid reactor 200, according to another embodiment. Ionic liquid reactor 200 may comprise a reactor top 202a, a reactor base, 202b, a reactor wall 220, a hydrocarbon vapor outlet 201, a plurality of hydrocarbon feed injection units 252, a plurality of ionic liquid injection nozzles 242, and a draft tube 230. Draft tube 230 may be disposed coaxially within ionic liquid reactor 200. In the embodiment of FIG. 13B, both the hydrocarbon feed injection units 252 and the ionic liquid injection nozzles 242 may be disposed within outer zone, OZ, of ionic liquid reactor 200.

Ionic liquid catalyst 42 may be introduced into ionic liquid reactor 200 via an ionic liquid injection conduit 240 in fluid communication with each of ionic liquid injection nozzles 242. A hydrocarbon feed stream 20 may be introduced into ionic liquid reactor 200 via a hydrocarbon feed injection conduit 250 in fluid communication with each of hydrocarbon feed injection units 252. In the embodiment of FIG. 13B, both the hydrocarbon feed injection units 252 and the ionic liquid injection nozzles 242 may be horizontally spaced apart.

Although the embodiment of FIG. 13B includes draft tube 230 within ionic liquid reactor 200, the configuration of hydrocarbon feed injection units 252 and ionic liquid injection nozzles 242 of FIG. 13B may also be used in the absence of a draft tube. In the embodiment of FIG. 13B, the general direction of flow of liquid reaction medium 21 within ionic liquid reactor 200 is indicated (arrows) as downward in inner zone, IZ, and upward in outer zone, OZ, i.e., the circulation of liquid reaction medium 21 may be generally reversed as compared with the embodiment of FIG. 13A.

FIG. 13C schematically represents a basal portion of a vertically oriented ionic liquid reactor 200, according to another embodiment. Ionic liquid reactor 200 may comprise a reactor top 202a, a reactor base, 202b, a reactor wall 220, a hydrocarbon vapor outlet 201, a plurality of hydrocarbon feed injection units 252, a plurality of ionic liquid injection nozzles 242, and a draft tube 230. Draft tube 230 may be disposed coaxially within ionic liquid reactor 200. In the embodiment of FIG. 13C, the hydrocarbon feed injection units 252 may be disposed within outer zone, OZ, of ionic liquid reactor 200, while ionic liquid injection nozzles 242 may be disposed within inner zone, IZ. Ionic liquid catalyst 42 may be introduced into ionic liquid reactor 200 via an ionic liquid injection conduit 240 in fluid communication with each of ionic liquid injection nozzles 242, e.g., as previously described. A hydrocarbon feed stream 20 may be introduced into ionic liquid reactor 200 via a hydrocarbon feed injection conduit 250 in fluid communication with each of hydrocarbon feed injection units 252.

In the embodiment of FIG. 13C, both the hydrocarbon feed injection units 252 and the ionic liquid injection nozzles 242 may be horizontally spaced apart. In the embodiment of FIG. 13C, the general direction of flow of liquid reaction medium 21 within ionic liquid reactor 200 is indicated (arrows) as upward in outer zone, OZ, and downward in inner zone, IZ. Although the embodiment of FIG. 13C includes draft tube 230 within ionic liquid reactor 200, the configuration of hydrocarbon feed injection units 252 and ionic liquid injection nozzles 242 of FIG. 13C may also be used in the absence of a draft tube.

FIG. 14A schematically represents a horizontally oriented ionic liquid reactor, and FIG. 14B shows the ionic liquid reactor of FIG. 14A as seen along the line 14B-14B according to another embodiment. In the embodiment of FIGS. 14A-14B, ionic liquid reactor 200 may be substantially cylindrical and may comprise a reactor top 202a, a reactor base, 202b, a reactor wall 220, and a hydrocarbon vapor outlet 201.

Ionic liquid reactor 200 of FIGS. 14A-14B may further comprise a plurality of hydrocarbon feed injection units 252. Hydrocarbon feed injection units 252 may be disposed in a lower or basal portion of ionic liquid reactor 200. Hydrocarbon feed injection units 252 may be horizontally spaced apart. Each hydrocarbon feed injection unit 252 may be in fluid communication with a hydrocarbon feed injection conduit 250. Each hydrocarbon feed injection unit 252 may be configured for injecting a hydrocarbon feed 20 into ionic liquid reactor 200 in an upward direction. In an embodiment, the hydrocarbon feed may comprise a combined feed stream, e.g., as described hereinabove with reference to FIG. 2. The injection of hydrocarbon feed 20 may promote hydrocarbon vaporization due to heat of reaction generated as a result of increased reaction rates adjacent to, e.g., above, each hydrocarbon feed injection unit 252, and such hydrocarbon vaporization may result in local turbulence of the liquid reaction medium in ionic liquid reactor 200. Such hydrocarbon vaporization may also cause upward flow of the liquid reaction medium above each hydrocarbon feed injection unit 252.

With further reference to FIGS. 14A-14B, ionic liquid reactor 200 may still further comprise an ionic liquid injection conduit 240 in fluid communication with each of a plurality of horizontally spaced ionic liquid injection nozzles 242, wherein each ionic liquid injection nozzle 242 may be configured for the injection of ionic liquid catalyst 42 into ionic liquid reactor 200. As shown, each ionic liquid injection nozzle 242 may be configured for the injection of ionic liquid catalyst 42 in a downward direction.

FIG. 15A schematically represents a horizontally oriented ionic liquid reactor, and FIG. 15B shows the ionic liquid reactor of FIG. 15A as seen along the line 15B-15B, according to another embodiment. In the embodiment of FIGS. 15A-15B, ionic liquid reactor 200 may have elements and features as described with reference to FIGS. 14A-14B, including a reactor top 202a, a reactor base, 202b, a reactor wall 220, hydrocarbon vapor outlet 201, a plurality of horizontally spaced ionic liquid injection nozzles 242, and a plurality of horizontally spaced hydrocarbon feed injection units 252.

With further reference to FIGS. 15A-15B, hydrocarbon feed injection units 252 may be disposed in a basal portion of ionic liquid reactor 200, and each hydrocarbon feed injection unit 252 may be configured for injecting a hydrocarbon feed 20 into ionic liquid reactor 200 in an upward direction. However, in the embodiment of FIGS. 15A-15B, ionic liquid injection nozzles 242 may be disposed in the basal portion of ionic liquid reactor 200, and each ionic liquid injection nozzle 242 may be configured for injecting ionic liquid catalyst into ionic liquid reactor 200 in an upward direction. Furthermore, in the embodiment of FIGS. 15A-15B ionic liquid injection nozzles 242 may be disposed in close proximity with, e.g., adjacent to, hydrocarbon feed injection units 252. The close proximity of ionic liquid injection nozzles 242 and hydrocarbon feed injection units 252 may promote efficient mixing of ionic liquid catalyst 42 with hydrocarbon feed 20 within ionic liquid reactor 200. Furthermore, injection of hydrocarbon feed 20 from each hydrocarbon feed injection unit 252 may promote hydrocarbon vaporization, turbulence within the liquid reaction medium, and an upward flow of the liquid reaction medium at locations above each hydrocarbon feed injection unit 252, substantially as described with reference to FIGS. 14A-14B, supra.

In an embodiment, systems as disclosed herein may be used for ionic liquid catalyzed alkylation processes. In an embodiment, the ionic liquid catalyst may comprise, e.g., a chloroaluminate ionic liquid as described hereinbelow. In an embodiment, a hydrocarbon feed stream for ionic liquid catalyzed alkylation may comprise at least one of an olefin feed stream, an isoparaffin feed stream, a condensed hydrocarbon liquid stream, an isobutane recycle stream, and a combined feed stream. Feedstocks, ionic liquid catalysts, and conditions for ionic liquid catalyzed alkylation are described generally hereinbelow.

Feedstocks for Ionic Liquid Catalyzed Alkylation

In an embodiment, feedstocks for ionic liquid catalyzed alkylation may comprise various olefin- and isoparaffin containing hydrocarbon streams in or from one or more of the following: a petroleum refinery, a gas-to-liquid conversion plant, a coal-to-liquid conversion plant, a naphtha cracker, a middle distillate cracker, a natural gas production unit, a LPG production unit, and a wax cracker, and the like.

Examples of olefin containing streams include FCC offgas, coker gas, olefin metathesis unit off-gas, polyolefin gasoline unit off-gas, methanol to olefin unit off-gas, FCC light naphtha, coker light naphtha, Fischer-Tropsch unit condensate, and cracked naphtha. Some olefin containing feed streams may contain at least one olefin selected from ethylene, propylene, butylenes, pentenes, and up to $C_{10}$ olefins, i.e., $C_2$-$C_{10}$ olefins, and mixtures thereof.

Examples of isoparaffin containing streams include, but are not limited to, FCC naphtha, hydrocracker naphtha, coker naphtha, Fisher-Tropsch unit condensate, natural gas condensate, and cracked naphtha. Such streams may comprise at least one $C_4$-$C_{10}$ isoparaffin. In an embodiment, such streams may comprise a mixture of two or more isoparaffins. In a sub-embodiment, an isoparaffin feed to the reactor during an ionic liquid catalyzed alkylation process may comprise isobutane.

Paraffin Alkylation

In an embodiment, the ionic liquid catalyzed alkylation of a mixture of hydrocarbons may be performed in a reactor vessel under conditions known to produce alkylate gasoline. The reactor may be referred to herein as an ionic liquid alkylation reactor, and the reactor may comprise at least one alkylation zone. The alkylation conditions in the alkylation reactor are selected to provide the desired product yields and quality. The alkylation reaction in the alkylation reactor is generally carried out in a liquid hydrocarbon phase, in a batch system, a semi-batch system, or a continuous system. The catalyst volume in the alkylation reactor may be in the range of 0.5 to 50 vol %, or from 1 to 20 vol %, or from 2 to 6 vol %. In an embodiment, mixing can be attained within the reactor, e.g., as described hereinabove, to provide contact between the hydrocarbon reactants and ionic liquid catalyst over a large surface area per unit volume of the reactor. The alkylation reaction temperature can be in the range from −10° C. to 50° C., such as 0° C. to 35° C., or 10° C. to 25° C. The alkylation pressure can be in the range from 0 to 1400 kPa, or from 0 to 700 kPa. In an embodiment, the alkylation pressure may be maintained at a level sufficient to keep the reactants at least partially in the liquid phase but sufficiently close to the boiling point of the reactants to allow vaporization of at least one hydrocarbon in the reactor by the reaction heat. The residence time of reactants in the reactor can be in the range from 1 to 60 minutes.

In one embodiment, the molar ratio of isoparaffin to olefin in the alkylation reactor can vary over a broad range. Generally the molar ratio of isoparaffin to olefin is in the range of from 5 to 15. For example, in different embodiments the molar ratio of isoparaffin to olefin may be from 5 to 15, from 7 to 12, or from 8 to 10. Lower isoparaffin to olefin molar ratios will tend to produce a higher yield of higher molecular weight alkylate products.

Ionic Liquid Catalysts for Hydrocarbon Conversion Processes

In an embodiment, a catalyst for hydrocarbon conversion processes, such as alkylation, may be a chloride-containing ionic liquid catalyst comprised of at least two components which form a complex. A first component of the chloride-containing ionic liquid catalyst can comprise a Lewis Acid selected from components such as Lewis Acidic compounds of Group 13 metals, including aluminum halides, alkyl aluminum halides, gallium halides, and alkyl gallium halides, indium halides, and alkyl indium halides (see International Union of Pure and Applied Chemistry (IUPAC), version 3, October 2005, for Group 13 metals of the periodic table). Other Lewis Acidic compounds, in addition to those of Group 13 metals, can also be used. In one embodiment the first component is aluminum halide or alkyl aluminum halide. For example, aluminum trichloride can be the first component of the chloride-containing ionic liquid catalyst.

A second component comprising the chloride-containing ionic liquid catalyst is an organic salt or mixture of salts. These salts can be characterized by the general formula $Q^+A^-$, wherein $Q^+$ is an ammonium, phosphonium, boronium, iodonium, or sulfonium cation and A− is a negatively charged ion such as $Cl^-$, $Br^-$, $ClO_4^-$, $NO_3^-$, $BF_4^-$, $BCl_4^-$, $PF_6^-$, $SbF_6^-$, $AlCl_4^-$, $TaF_6^-$, $CuCl_2^-$, $FeCl_3^-$, $HSO_3^-$, $RSO_3^-$ (wherein R is an alkyl group having from 1 to 12 carbon atoms), $SO_3CF_3^-$, and 3-sulfurtrioxyphenyl. In one embodiment, the second component is selected from those having quaternary ammonium or phosphonium halides containing one or more alkyl moieties having from 1 to 12 carbon atoms, such as, for example, trimethylamine hydrochloride, methyltributylammonium halide, trialkylphosphonium hydrochloride, tetraalkylphosphonium chlorides, methyltrialkylphosphonium halide or substituted heterocyclic ammonium halide compounds, such as hydrocarbyl substituted pyridinium halide compounds, for example, 1-butylpyridinium halide, benzylpyridinium halide, or hydrocarbyl substituted imidazolium halides, such as for example, 1-ethyl-3-methyl-imidazolium chloride.

In one embodiment the chloride-containing ionic liquid catalyst is selected from the group consisting of hydrocarbyl substituted pyridinium chloroaluminate, hydrocarbyl substituted imidazolium chloroaluminate, quaternary amine chloroaluminate, trialkyl amine hydrogen chloride chloroaluminate, alkyl pyridine hydrogen chloride chloroaluminate, and mixtures thereof. For example, the chloride-containing ionic liquid catalyst can be an acidic haloaluminate ionic liquid, such as an alkyl substituted pyridinium chloroaluminate or an alkyl substituted imidazolium chloroaluminate of the general formulas A and B, respectively.

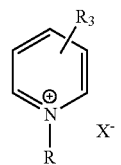

A

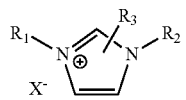

B

In the formulas A and B, R, $R_1$, $R_2$, and $R_3$ are H, methyl, ethyl, propyl, butyl, pentyl or hexyl group, and X is a chloroaluminate. In the formulas A and B, R, $R_1$, $R_2$, and $R_3$ may or may not be the same. In one embodiment the chloride-containing ionic liquid catalyst is N-butylpyridinium chloroaluminate. Examples of highly acidic chloroaluminates are $Al_2Cl_7^-$ and $Al_3Cl_{10}^-$.

In another embodiment the chloride-containing ionic liquid catalyst can have the general formula RR'R"NH$^+$ $Al_2Cl_7^-$, wherein R, R', and R" are alkyl groups containing from 1 to 12 carbons, and where R, R', and R" may or may not be the same.

In another embodiment the chloride-containing ionic liquid catalyst can have the general formula RR'R"R'"P$^+$ $Al_2Cl_7^-$, wherein R, R', R" and R'" are alkyl groups containing from 1 to 12 carbons, and where R, R', R" and R'" may or may not be the same.

The presence of the first component should give the chloride-containing ionic liquid a Lewis or Franklin acidic character. Generally, the greater the mole ratio of the first component to the second component, the greater is the acidity of the chloride-containing ionic liquid catalyst. The molar ratio of the first component (metal halide) to the second component (quaternary amine or quaternary phosphorus) is in the range of 2:1 to 1.1:1.

In one embodiment, the chloride-containing ionic liquid catalyst is mixed in the alkylation reactor with a hydrogen halide and/or an organic halide. The hydrogen halide or organic halide can boost the overall acidity and change the selectivity of the chloride-containing ionic liquid catalyst. The organic halide can be an alkyl halide. The alkyl halides that can be used include alkyl bromides, alkyl chlorides, alkyl iodides, and mixtures thereof. A variety of alkyl halides can be used. Alkyl halide derivatives of the isoparaffins or the olefins that comprise the feed streams in the alkylation process are good choices. Such alkyl halides include, but are not limited to, isopentyl halides, isobutyl halides, butyl halides (e.g., 1-butyl halide or 2-butyl halide), propyl halides and ethyl halides. Other alkyl chlorides or halides having from 1 to 8 carbon atoms can be also used. The alkyl halides can be used alone or in combination or with hydrogen halide. The alkyl halide or hydrogen halide is fed to the unit by injecting the alkyl halide or hydrogen halide to the hydrocarbon feed, or to the ionic liquid catalyst or to the alkylation reactor directly. The amount of HCl or alkyl chloride usage, the location of the injection and the injection method may affect the amount of organic chloride side-product formation. The use of alkyl halides to promote hydrocarbon conversion by chloride-containing ionic liquid catalysts is taught in U.S. Pat. No. 7,495,144 and in U.S. Patent Publication No. 20100298620A1.

It is believed that the alkyl halide decomposes under hydrocarbon conversion conditions to liberate Bronsted acids or hydrogen halides, such as hydrochloric acid (HCl) or hydrobromic acid (HBr). These Bronsted acids or hydrogen halides promote the hydrocarbon conversion reaction. In one embodiment the halide in the hydrogen halide or alkyl halide is chloride. In one embodiment the alkyl halide is an alkyl chloride, for example t-butyl chloride. Hydrogen chloride and/or an alkyl chloride can be used advantageously, for example, when the chloride-containing ionic liquid catalyst is a chloroaluminate.

Ionic Liquid Catalyst Regeneration

As a result of use, ionic liquid catalysts become deactivated, i.e. lose activity, and may eventually need to be replaced. However, ionic liquid catalysts are expensive and replacement adds significantly to operating expenses. Thus it may be desirable to regenerate the ionic liquid catalyst.

The regeneration of acidic ionic liquid catalysts is taught, for example, by U.S. Pat. Nos. 7,651,970, 7,674,739, 7,691,771, 7,732,363, and 7,732,364.

Alkylation processes utilizing an ionic liquid catalyst may generate by-products known as conjunct polymers. These conjunct polymers are highly unsaturated molecules and deactivate the ionic liquid catalyst by forming complexes with the ionic liquid catalyst. A portion of used ionic liquid catalyst from the alkylation reactor is sent to the regenerator reactor which removes the conjunct polymer from the ionic liquid catalyst and recovers the activity of the ionic liquid catalyst. The regeneration reactor contains metal components that saturates the conjunct polymers and releases the saturated polymer molecules from the ionic liquid catalyst. The regeneration can be performed either in a stirred reactor or a fixed bed reactor. A guard bed vessel containing adsorbent material with appropriate pore size may be added before the regeneration reactor to minimize contaminants going into the regeneration reactor.

Product Separation and Finishing

A hydrocarbon effluent from the reactor may contain trace amounts of hydrogen halides or organic halides or inorganic halides. When aluminum chloride containing catalyst is used, then trace amounts of HCl, organic chlorides and inorganic chlorides may be present in the reactor effluent. HCl and organic chlorides may be captured and recycled to the alkylation reactor. Inorganic chlorides such as corrosion products or decomposition product may be captured with a filter.

The separated hydrocarbon product may still contain trace amounts of HCl, organic chlorides and inorganic chlorides. Removal of HCl and inorganic chlorides from the product are typically done by caustic washing. Chloride selective adsorbent may be used to capture the residual chlorides. Organic chloride may be converted to HCl and organic hydrocarbon by hydrogenation, cracking or hot caustic treating. Treating of products for chloride reduction is taught, for example, in U.S. Pat. Nos. 7,538,256, 7,955,498, and 8,327,004.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

All publications, patents, and patent applications cited in this application are herein incorporated by reference in their entirety to the same extent as if the disclosure of each individual publication, patent application, or patent was specifically and individually indicated to be incorporated by reference in its entirety.

The drawings are representational and may not be drawn to scale. Modifications of the exemplary embodiments disclosed above may be apparent to those skilled in the art in light of this disclosure. Accordingly, the invention is to be construed as including all structure and methods that fall within the scope of the appended claims. Unless otherwise specified, the recitation of a genus of elements, materials or other components, from which an individual component or mixture of components can be selected is intended to include all possible sub-generic combinations of the listed components and mixtures thereof.

It is claimed:

1. A process, comprising:
   a) contacting a hydrocarbon feed stream comprising at least one isoparaffin and at least one olefin with an ionic liquid catalyst in an ionic liquid alkylation zone under ionic liquid alkylation conditions to perform an exothermic ionic liquid alkylation reaction wherein the at least one isoparaffin and the at least one olefin are alkylated;
   b) via a heat of reaction of the exothermic ionic liquid alkylation reaction, vaporizing a portion of at least one hydrocarbon in the ionic liquid alkylation zone to provide a hydrocarbon vapor in the ionic liquid alkylation zone;
   c) withdrawing at least a portion of the hydrocarbon vapor from the ionic liquid alkylation zone;
   d) condensing a withdrawn portion of the hydrocarbon vapor from step c) to provide a condensed hydrocarbon liquid stream; and
   e) recycling the condensed hydrocarbon liquid stream to the ionic liquid alkylation zone; wherein the hydrocarbon feed stream is injected into an outer zone that is external to a draft tube disposed vertically within the ionic liquid alkylation zone.

2. The process according to claim 1, wherein:
   step c) comprises withdrawing at least the portion of the hydrocarbon vapor from a top portion of the ionic liquid alkylation zone, wherein bubbles of the hydrocarbon vapor have disengaged from a liquid reaction medium in the top portion of the ionic liquid alkylation zone,
   step d) comprises cooling the withdrawn portion of the hydrocarbon vapor via a heat exchanger disposed downstream from the ionic liquid alkylation zone, and the process further comprises:
   f) prior to step d), removing any entrained droplets of ionic liquid from the withdrawn second portion of the hydrocarbon vapor.

3. The process according to claim 1, wherein:
   step d) comprises cooling the withdrawn portion of the hydrocarbon vapor via a heat exchanger, and the process further comprises:
   g) adjusting a coolant flow rate to the heat exchanger so as to control a temperature of the ionic liquid alkylation zone.

4. The process according to claim 1, wherein:
   the withdrawn portion of the hydrocarbon vapor comprises a propane, and
   step e) comprises recycling the propane to the ionic liquid alkylation zone via the condensed hydrocarbon liquid stream.

5. The process according to claim 1, wherein step e) comprises recycling the condensed hydrocarbon liquid stream to the ionic liquid alkylation zone without any fractionation of the condensed hydrocarbon liquid stream.

6. The process according to claim 1, wherein:
   the ionic liquid alkylation zone contains a liquid reaction medium comprising droplets of the ionic liquid catalyst dispersed in a liquid hydrocarbon phase,
   step b) comprises forming bubbles of the hydrocarbon vapor within the liquid reaction medium, and the process further comprises:
   h) pneumatically agitating the liquid reaction medium via the bubbles of the hydrocarbon vapor.

7. The process according to claim 1, wherein:
   the hydrocarbon feed stream comprises a combined feed stream, and
   step e) comprises merging the condensed hydrocarbon liquid stream with an olefin feed stream, and with an isobutane recycle stream obtained by fractionating a hydrocarbon phase separated from a reactor effluent from the ionic liquid alkylation zone, to provide the combined feed stream.

8. The process according to claim 7, wherein:
   the exothermic ionic liquid alkylation reaction occurs in a liquid phase,
   the combined feed stream comprises at least one $C_3$-$C_4$ alkane, and
   the ionic liquid alkylation conditions are selected to promote a vaporization of the at least one $C_3$-$C_4$ alkane only in the presence of the exothermic ionic liquid alkylation reaction.

9. The process according to claim 7, further comprising:
   i) injecting the combined feed stream, via at least one hydrocarbon feed injection unit, in an upward direction into the outer zone of the ionic liquid alkylation zone.

10. The process according to claim 9, wherein the withdrawn portion of the hydrocarbon vapor is equal to 5-50 mol % of the combined feed stream injected into the outer zone of the ionic liquid alkylation zone in step i).

11. The process according to claim 9, wherein:
    the ionic liquid alkylation zone contains a liquid reaction medium comprising droplets of the ionic liquid catalyst dispersed in a liquid hydrocarbon phase, and
    a vaporization of the at least one hydrocarbon in the outer zone of the ionic liquid alkylation zone causes upward flow of the liquid reaction medium within the outer zone of the ionic liquid alkylation zone at a location above the at least one hydrocarbon feed injection unit.

12. The process according to claim 11, wherein:
    the draft tube defines an inner zone within the draft tube,
    the inner zone and the outer zone each contain the liquid reaction medium,
    the liquid reaction medium flows generally upward in the outer zone, and the liquid reaction medium flows generally downward within the draft tube.

13. The process according to claim 1, further comprising:
    j) injecting the ionic liquid catalyst into the outer zone of the ionic liquid alkylation zone via at least one ionic liquid injection nozzle.

14. The process according to claim 1, further comprising:
    k) injecting the ionic liquid catalyst into an inner zone of the ionic liquid alkylation zone, wherein the internal zone is internal to the draft tube, via at least one ionic liquid injection nozzle.

15. The process according to claim 1, further comprising:
    l) withdrawing a liquid reaction medium from a basal portion of the ionic liquid alkylation zone, wherein the liquid reaction medium comprises the ionic liquid catalyst; and
    m) recycling a withdrawn liquid reaction medium to the ionic liquid alkylation zone via a plurality of ionic liquid injection nozzles.

16. The process according to claim 1, wherein the draft tube includes an enlarged upper portion that promotes a vapor bubble disengagement from a liquid reaction medium in an upper portion of the ionic liquid alkylation zone.

17. The process according to claim 1, wherein the exothermic ionic liquid alkylation reaction occurs in an ionic liquid reactor operated with no moving parts.

18. A process, comprising:
a) contacting a hydrocarbon feed stream comprising at least one isoparaffin and at least one olefin with an ionic liquid catalyst in an ionic liquid alkylation zone under ionic liquid alkylation conditions to perform an exothermic ionic liquid alkylation reaction, wherein the ionic liquid alkylation zone contains a liquid reaction medium comprising droplets of the ionic liquid catalyst dispersed in a liquid hydrocarbon phase;
b) via a heat of reaction of the exothermic ionic liquid alkylation reaction, vaporizing a portion of at least one hydrocarbon in the ionic liquid alkylation zone to form bubbles of a hydrocarbon vapor within the liquid reaction medium;
c) via the bubbles of the hydrocarbon vapor, pneumatically agitating the liquid reaction medium in the ionic liquid alkylation zone;
d) withdrawing at least a portion of the hydrocarbon vapor from the ionic liquid alkylation zone;
e) condensing a withdrawn portion of the hydrocarbon vapor from step d) to provide a condensed hydrocarbon liquid stream; and
f) recycling the condensed hydrocarbon liquid stream to the ionic liquid alkylation zone; wherein the hydrocarbon feed stream is injected into an outer zone that is external to a draft tube disposed vertically within the ionic liquid alkylation zone.

19. The process according to claim 18, wherein:
the condensed hydrocarbon liquid stream comprises a $C_3$-$C_4$ hydrocarbon selected from the group consisting of propane, isobutane, n-butane, and combinations thereof, and step f) comprises:
g) combining the condensed hydrocarbon liquid stream, en masse, with an olefin feed stream and an isobutane recycle stream to provide a combined feed stream; and
h) injecting the combined feed stream into the outer zone of the ionic liquid alkylation zone via at least one hydrocarbon feed injection unit.

20. The process according to claim 19, wherein:
at least a third portion of the bubbles of the hydrocarbon vapor rise through the liquid reaction medium to a top portion of the ionic liquid alkylation zone, and
the liquid reaction medium flows upward within the ionic liquid alkylation zone at a location above each said at least one hydrocarbon feed injection unit.

21. The process according to claim 19, further comprising:
i) injecting the ionic liquid catalyst into the ionic liquid alkylation zone via a plurality of ionic liquid injection nozzles, and wherein step h) comprises injecting the combined feed stream into the outer zone of the ionic liquid alkylation zone in an upward direction.

22. The process according to claim 18, wherein the draft tube includes an enlarged upper portion that promotes a vapor bubble disengagement from the liquid reaction medium in an upper portion of the ionic liquid alkylation zone.

23. The process according to claim 18, wherein the exothermic ionic liquid alkylation reaction occurs in an ionic liquid reactor operated with no moving parts.

24. A process, comprising:
a) injecting a combined feed stream into an outer zone that is external to a draft tube disposed vertically within an ionic liquid alkylation zone, wherein the combined feed stream comprises at least one $C_4$-$C_{10}$ isoparaffin and at least one $C_2$-$C_{10}$ lefin;
b) injecting an ionic liquid catalyst into the ionic liquid alkylation zone via at least one ionic liquid injection nozzle;
c) contacting the at least one $C_4$-$C_{10}$ isoparaffin and the at least one $C_2$-$C_{10}$ olefin with the ionic liquid catalyst in the outer zone of the ionic liquid alkylation zone under ionic liquid alkylation conditions to perform an exothermic ionic liquid alkylation reaction in a liquid reaction medium;
d) via a heat of reaction of the exothermic ionic liquid alkylation reaction, vaporizing a portion of at least one hydrocarbon component of the combined feed stream to provide a hydrocarbon vapor in the outer zone of the ionic liquid alkylation zone;
e) withdrawing at least a portion of the hydrocarbon vapor from the ionic liquid alkylation zone, wherein the hydrocarbon vapor comprises a $C_3$-$C_4$ hydrocarbon selected from the group consisting of propane, isobutane, n-butane, and combinations thereof;
f) condensing a withdrawn portion of the hydrocarbon vapor to provide a condensed hydrocarbon liquid stream;
g) merging the condensed hydrocarbon liquid stream with an olefin feed stream and an isobutane recycle stream to provide the combined feed stream;
h) withdrawing aliquots of the liquid reaction medium from the ionic liquid alkylation zone to provide a reactor effluent stream;
i) separating the reactor effluent stream into an ionic liquid phase and a hydrocarbon phase; and
j) fractionating the hydrocarbon phase to provide the isobutane recycle stream and an alkylate product.

25. The process according to claim 24, wherein:
step d) comprises forming bubbles of the hydrocarbon vapor within the liquid reaction medium, wherein at least a third portion of the bubbles of the hydrocarbon vapor rise through the liquid reaction medium to a top portion of the ionic liquid alkylation zone,
step e) comprises withdrawing the hydrocarbon vapor from the top portion of the ionic liquid alkylation zone, and the process further comprises:
k) pneumatically agitating the liquid reaction medium via the bubbles of the hydrocarbon vapor.

26. The process according to claim 24, wherein the draft tube includes an enlarged upper portion that promotes a vapor bubble disengagement from the liquid reaction medium in an upper portion of the ionic liquid alkylation zone.

27. A process, comprising:
a) contacting a hydrocarbon feed stream comprising at least one isoparaffin and at least one olefin with an ionic liquid catalyst in an ionic liquid alkylation zone under ionic liquid alkylation conditions to perform an exothermic ionic liquid alkylation reaction wherein the at least one isoparaffin and the at least one olefin are alkylated;
b) via a heat of reaction of the exothermic ionic liquid alkylation reaction, vaporizing a portion of at least one hydrocarbon in the ionic liquid alkylation zone to provide a hydrocarbon vapor in the ionic liquid alkylation zone;
c) withdrawing at least a portion of the hydrocarbon vapor from the ionic liquid alkylation zone;

d) condensing a withdrawn portion of the hydrocarbon vapor from step c) to provide a condensed hydrocarbon liquid stream; and
e) recycling the condensed hydrocarbon liquid stream to the ionic liquid alkylation zone; wherein the exothermic ionic liquid alkylation reaction occurs in an ionic liquid reactor with a draft tube disposed vertically therein and the ionic liquid reactor operates with no moving parts.

* * * * *